US007925064B2

(12) United States Patent
Cloutier et al.

(10) Patent No.: US 7,925,064 B2
(45) Date of Patent: Apr. 12, 2011

(54) AUTOMATIC MULTI-DIMENSIONAL INTRAVASCULAR ULTRASOUND IMAGE SEGMENTATION METHOD

(75) Inventors: Guy Cloutier, Repentigny (CA); Marie-Hélène Roy-Cardinal, Montréal (CA); Jean Meunier, Outremont (CA); Gilles Soulez, Outremont (CA); Eric Therasse, Montréal (CA)

(73) Assignees: Val-Chum, Limited Partnership, Montreal, Quebec (CA); Valorisation-Recherche, Limited Partnership, Montreal, Quebec (CA)

( * ) Notice: Subject to any disclaimer, the term of this patent is extended or adjusted under 35 U.S.C. 154(b) by 1101 days.

(21) Appl. No.: 10/579,381

(22) PCT Filed: Nov. 15, 2004

(86) PCT No.: PCT/CA2004/001970
§ 371 (c)(1),
(2), (4) Date: Feb. 6, 2007

(87) PCT Pub. No.: WO2005/048190
PCT Pub. Date: May 26, 2005

(65) Prior Publication Data
US 2007/0165916 A1    Jul. 19, 2007

(30) Foreign Application Priority Data
Nov. 13, 2003  (CA) .................................... 2449080

(51) Int. Cl.
*G06K 9/00* (2006.01)
(52) U.S. Cl. ...................................................... 382/128
(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS

| 4,794,931 | A  | 1/1989  | Yock ............................. 600/439 |
| 5,559,901 | A  | 9/1996  | Lobregt ........................ 382/256 |
| 5,771,895 | A  | 6/1998  | Slager .......................... 600/462 |
| 5,830,145 | A  | 11/1998 | Tenhoff ........................ 600/463 |
| 6,381,350 | B1 | 4/2002  | Klingensmith et al. ...... 382/128 |
| 6,496,181 | B1 | 12/2002 | Bomer et al. ................. 345/167 |

(Continued)

FOREIGN PATENT DOCUMENTS

EP   1227342   7/2002
(Continued)

OTHER PUBLICATIONS

Antiga et al., "Computational Geometry for Patient Specific Reconstruction and Meshing of Blood Vessels from MR and CT Angiography," *IEEE Transactions on Medical Imaging*, 22:674-684, 2003.

(Continued)

*Primary Examiner* — Samir A Ahmed
*Assistant Examiner* — Atiba O Fitzpatrick
(74) *Attorney, Agent, or Firm* — Fulbright & Jaworski L.L.P.

(57) ABSTRACT

The present invention generally relates to intravascular ultrasound (IVUS) image segmentation methods, and is more specifically concerned with an intravascular ultrasound image segmentation method for characterizing blood vessel vascular layers. The proposed image segmentation method for estimating boundaries of layers in a multi-layered vessel provides image data which represent a plurality of image elements of the multi-layered vessel. The method also determines a plurality of initial interfaces corresponding to regions of the image data to segment and further concurrently propagates the initial interfaces corresponding to the regions to segment. The method thereby allows to estimate the boundaries of the layers of the multi-layered vessel by propagating the initial interfaces using a fast marching model based on a probability function which describes at least one characteristic of the image elements.

31 Claims, 14 Drawing Sheets

U.S. PATENT DOCUMENTS

| | | | |
|---|---|---|---|
| 6,718,193 B2 | 4/2004 | Knoplioch et al. | 600/407 |
| 2003/0053667 A1 | 3/2003 | Paragios et al. | 382/128 |
| 2003/0118221 A1 | 6/2003 | Deschamps et al. | 382/128 |
| 2003/0197704 A1 | 10/2003 | Tek et al. | 345/474 |
| 2004/0019267 A1 | 1/2004 | Paragios et al. | 600/407 |
| 2004/0024315 A1 | 2/2004 | Chalana et al. | 600/443 |
| 2007/0216678 A1 | 9/2007 | Rouet et al. | 382/154 |

FOREIGN PATENT DOCUMENTS

| | | |
|---|---|---|
| EP | 1306803 | 5/2003 |
| JP | 10-137238 | 5/1998 |
| JP | 2003-503141 | 1/2003 |
| WO | WO 99/13432 | 3/1999 |
| WO | WO 00/19904 | 4/2000 |
| WO | WO 03/041584 | 5/2003 |
| WO | WO 04/001671 | 12/2003 |
| WO | WO 2004/079654 | 9/2004 |

OTHER PUBLICATIONS

Boukerroui et al., "Segmentation of ultrasound images- multiresolution 2D and 3D algorithm based on global and local statistics," *Pattern Recognition Letters*, 24:779-790, 2003.

Bovenkamp et al., "Multi-Agent IVUS Image Interpretation," *SPIE Proceedings: Medical Imaging 2003: Image Processing*, 5032:619-630, 2003.

Bruining et al., "ECG-gated versus nongated three-dimensional intracoronary ultrasound analysis: implications for volumetric measurements," *Catheterization and Cardiovascular Diagnosis*, 43:254-260, 1998.

Brusseau et al., "Fully Automatic Luminal Contour Segmentation in Intracoronary Ultrasound Imaging- A Statistical Approach," *IEEE Trans. Med. Imag.*, 23:554-566, 2004.

Cardinal et al., "Intravascular Ultrasound Image Segmentation: A Fast-Marching Method," *Lecture Notes in Computer Science*, 2879:432-439, 2003.

Chalana and Kim, "A Methodology for Evaluation of Boundary Detection Algorithms on Medical Images," *IEEE Trans. Med. Imag.*, 16:642-652, 1997.

Colombo et al., "Intracoronary Stenting Without Anticoagulation Accomplished With Intravascular Ultrasound Guidance," *Circulation*, 91:1676-1688, 1995.

De Korte et al., "Intravascular elasticity imaging using ultrasound: feasibility studies in phantoms," *Ultrasound Med. Biol.*, 23:735-746, 1997.

De Winter et al., "Retrospective Image-Based Gating of Intracoronary Ultrasound Images for Improved Quantitative Analysis: The Intelligate Method," *Characterization and Cardiovascular Diagnosis*, 61:84-94, 2004.

Delignon et al., "Estimation of Generalized Mixtures and Its Application in Image Segmentation," *IEEE Transactions on Image Processing*, 6:1364-1375, 1997.

Dempster et al., "Maximum Likelihood from Incomplete Data via the EM Algorithm," *J. Roy. Stat. Soc. B*, 39:1-38, 1977.

Dutt and Greenleaf, "Statistics of the log-compressed echo envelope," *J. Acoust. Soc. Am.*, 99:3817-3825, 1996.

Gussenhoven et al., "Arterial Wall Characteristics Determined by Intravascular Ultrasound Imaging: An in Vitro Study," *J. Am. Coll. Cardiol.*, 14:947-952, 1989.

Haas et al., "Segmentation of 3D intravascular ultrasonic images based on a random field model," *Ultrasound Med. Biol.*, 26:297-306, 2000.

Hagenaars et al., "Gamma radiation induces positive vascular remodeling after balloon angioplasty: a prospective, randomized intravascular ultrasound scan study," *Journal of Vascular Surgery*, 36:318-324, 2002.

Han et al., "A Fast Minimal Path Active Contour Model," *IEEE Transactions on Image Processing*, 10:865-873, 2001.

Hastie et al., The Elements of Statistical Learning: Data Mining, Inference, and Prediction, Springer, New York, pp. 236-243, 2001.

Jain et al., "Deformable template models: A review," *Signal Processing*, 71:109-129, 1998.

Kallel et al., "Speckle Motion Artifact Under Tissue Rotation," *IEEE Trans. Ultrason., Ferroelect., Freq. Contr.*, 41:105-122, 1994.

Klingensmith et al., "Evaluation of Three-Dimensional Segmentation Algorithms for the Identification of Luminal and Medial-Adeventitial Borders in Intravascular Ultrasound Images," *IEEE Trans. Med. Imag.*, 19:996-1011, 2000.

Koning et al., "Advanced contour detection for three-dimensional intracoronary ultrasound: a validation- in vitro and in vivo," *Int. J. Cardiovascular Imaging*, 18:235-248, 2002.

Kovalski et al., "Three-dimensional automatic quantitative analysis of intravascular ultrasound images," *Ultrasound Med. Biol.*, 26:527-537, 2000.

Malladi et al., "Shape Modeling with Front Propagation: A Level Set Approach," *IEEE Trans. Pattern Anal. Machine Intell.*, 17:158-175, 1995.

Maurice et al., "Adapting the Lagrangian speckle model estimator for endovascular elastography: theory and validation with simulated radio-frequency data," *J. Acoust. Soc. Am.*, 116:1276-1286, 2004.

Mignotte and Meunier, "A multiscale optimization approach for the dynamic contour-based boundary detection issue," *Computerized Medical Imaging and Graphics*, 25:265-275, 2001.

Mintz et al., "American College of Cardiology Clinical Expert Consensus Document on Standards for Acquisition, Measurement and Reporting of Intravascular Ultrasound Studies (IVUS). A report of the American College of Cardiology Task Force on Clinical Expert Consensus Documents," *J. Am. Coll. Cardiol.*, 37:1478-1492, 2001.

Mintz et al., "Atherosclerosis in angiographically "normal"coronary artery reference segments: an intravascular ultrasound study with clinical correlations," *J. Am. Coll. Cardiol.*, 25:1479-1485, 1995.

Mojsilovic et al., "Automatic segmentation of intravascular ultrasound images: a texture-based approach," *Ann. Biomed. Eng.*, 25:1059-1071, 1997.

Nadkarni et al., "Image-based Retrospective Cardiac Gating for Three-Dimensional Intravascular Ultrasound Imaging," *SPIE Proceedings: Medical Imaging: Ultrasonic Imaging and Signal Processing*, 4687:276-284, 2002.

Nissen and Yock, "Intravascular Ultrasound: Novel Pathophysiological Insights and Current Clinical Applications," *Circulation*, 103:604-616, 2001.

Nissen, "Application of Intravascular Ultrasound to Characterize Coronary Artery Disease and Assess the Progression or Regression of Atherosclerosis," *Am. J. Cardiol.*, 89:24B-31B, 2002.

Osher and Sethian, "Fronts Propagating with Curvature Dependent Speed: Algorithms Based on Hamilton-Jacobi Formulations," *J. Comput. Phys.*, 79:12-49, 1988.

Pieczynski, "Hidden Markov Fields and Iterative Conditional Estimation," *Traitement du Signal*, 11:141-153, 1994 (English Abstract).

Pujol et al., "Intravascular Ultrasound Images Vessel Characterization using AdaBoost," *Lecture Notes in Computer Science*, 2674:242-251, 2003.

Sethian, "A fast marching level set method for monotonically advancing fronts," *Proceedings of the National Academy of the Sciences USA*, 93:1591-1595, 1996.

Sethian, In: Level Set Methods and Fast Marching Methods: Evolving Interfaces in Computational Geometry, Fluids Mechanics, Computer Vision and Materials Science, $2^{nd}$ ed., Cambridge University Press, 1999.

Shankar, "A General Statistical Model for Ultrasonic Backscattering from Tissues," *IEEE Transactions on Ultrasonics, Feroelectronics, and Freq. Control*, 47:727-736, 2000.

Shaw et al., "Determinants of Coronary Artery Compliance in Subjects With and Without Angiographic Coronary Artery Disease," *J American College of Cardiology*, 39:1637-1643, 2002.

Sifakis et al., "Bayesin Level Sets for Image Segmentation," *J. Visual Commun. Imag. Rep.*, 13:44-64, 2002.

Tai et al., "In vivo femoropopliteal arterial wall compliance in subjects with and without lower limb vascular disease," *J. Vascular Surgery*, 30:936-945, 1999.

Takano et al., "Mechanical and Structural Characteristics of Vulnerable Plaques: Analysis by Coronary Angioscopy and Intravascular Ultrasound," *J American College of Cardiology*, 38:99-104, 2001.

Von Birgelen et al., "ECG-Gated Three-dimensional Intravascular Ultrasound," *Circulation*, 96:2944-2952, 1997.

Von Birgelen et al., "Morphometric analysis in three-dimensional intracoronary ultrasound: an in vitro and in vivo study performed with a novel system for the contour detection of lumen and plaque," *Am. Heart J.*, 132:516-527, 1996.

Wagner et al., "Statistics of Speckle in Ultrasound B-Scans," *IEEE Transactions on Sonics and Ultrasonics*, 30:156-163, 1983.

Wear et al., "Statistical properties of estimates of signal-to-noise ratio and number of scatterers per resolution cell," *Journal of the Acoustical Society of America*, 102:635-641, 1997.

Weichert et al., "Virtual 3D IVUS vessel model for intravascular brachytherapy planning. I. 3D segmentation, reconstruction, and visualization of coronary artery architecture and orientation," *Med. Phys.*, 30:2530-2536, 2003.

Xu et al., "Image Segmentation Using Deformable Models," Handbook of Medical Imaging, vol. 2: Medical Image Processing and Analysis, Sonka and Fitzpatrick (eds.), SPIE Press, 2000.

Zhang et al., "Tissue Characterization in Intravascular Ultrasound Images," *IEEE Trans. Med. Imag.*, 17:889-899, 1998.

Zhong et al., "Object Tracking Using Deformable Templates," Sixth International Conference on Computer Vision, pp. 410-445, 1998.

Zhu et al., "Retrieval of Cardiac Phase from IVUS Sequences," *SPIE Proceedings: Medical Imaging: Ultrasonic Imaging and Signal Processing*, 5035:135-146, 2003.

Supplementary European Search Report, issued in European Application No. EP 04818371, dated May 30, 2008.

Bühler et al., "Geometric methods for vessel visualization and quantification—A survey," *Technical Report VRVIS Research Center*, Vienna Austria, http://www.vrvis.at/TR/2002/TR_VRVis_2002_035_Full.pdf, 2002.

Rotger et al., "Multimodal registration of intravascular ultrasound images and angiography," *Proceedings of the XX Congreso Annual De La Sociedad Espanola De Ingenieria Biomedica*, http://www.cvc.uab.es/~petia/david_zaragoza_2002.pdf, 2002.

Zhu et al., "IVUS Image segmentation based on contrast," *Proceedings of the SIOE—The International Society for Optical Engineering SPIE-INT Soc. Opt. Eng. USA*, 4684: 1721-1733, 2002.

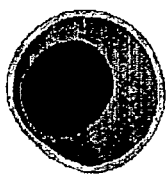 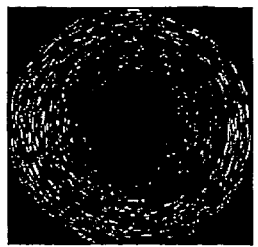 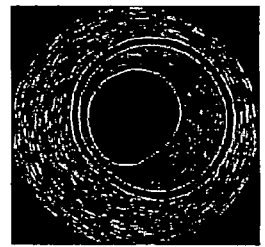 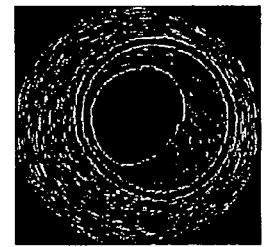
FIGURE 7A    FIGURE 7B    FIGURE 7C    FIGURE 7D
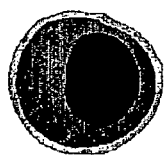 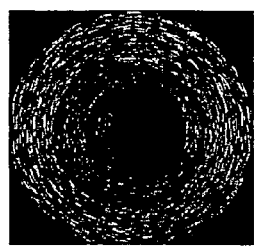 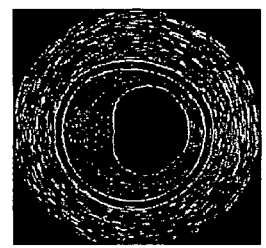 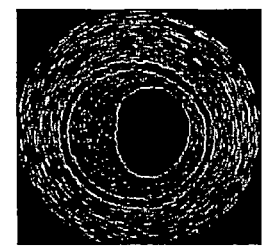
FIGURE 8A    FIGURE 8B    FIGURE 8C    FIGURE 8D

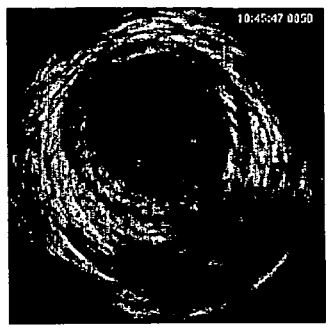 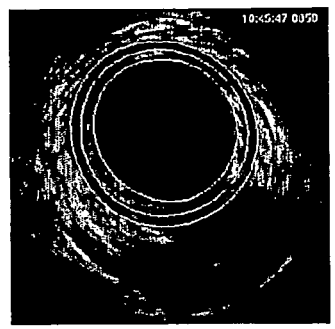 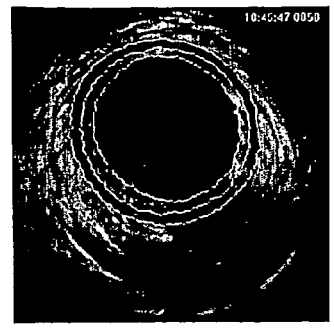
FIGURE 9A  FIGURE 9B  FIGURE 9C
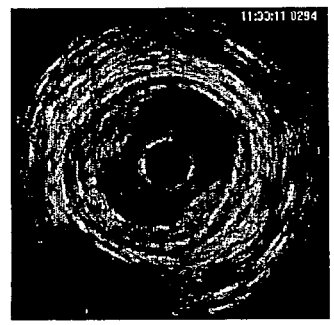 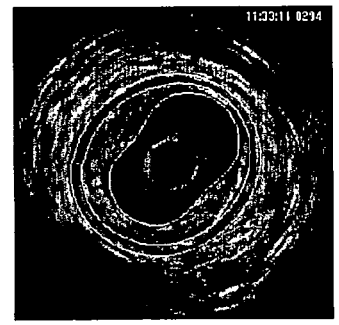 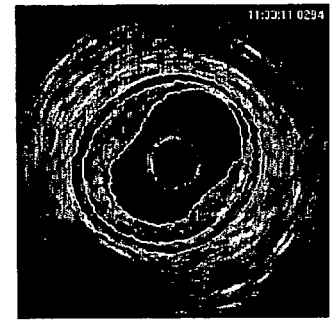
FIGURE 10A  FIGURE 10B  FIGURE 10C
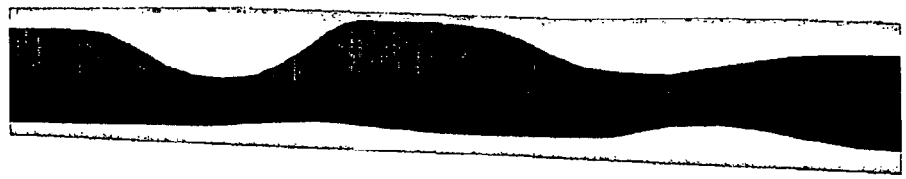
FIGURE 11

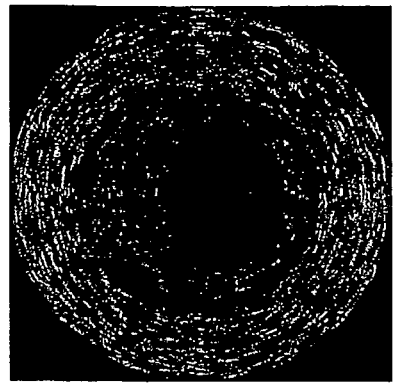
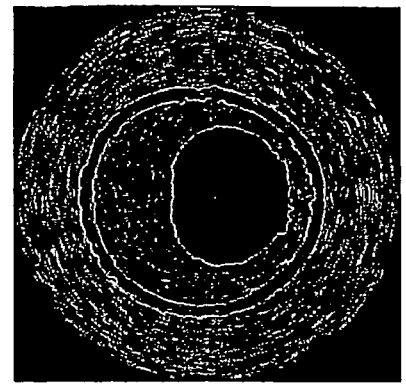
FIGURE 12A          FIGURE 12B
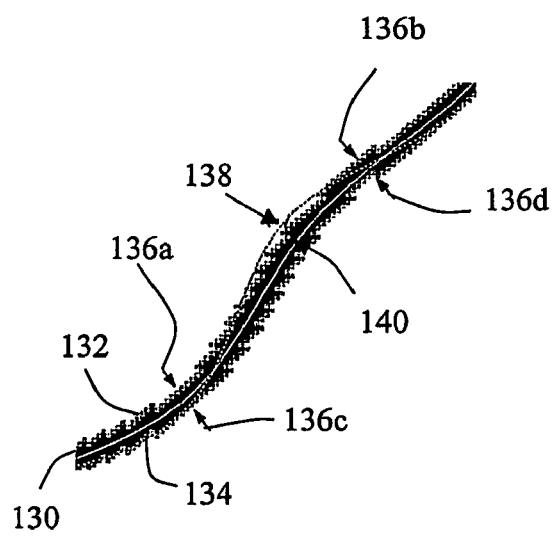
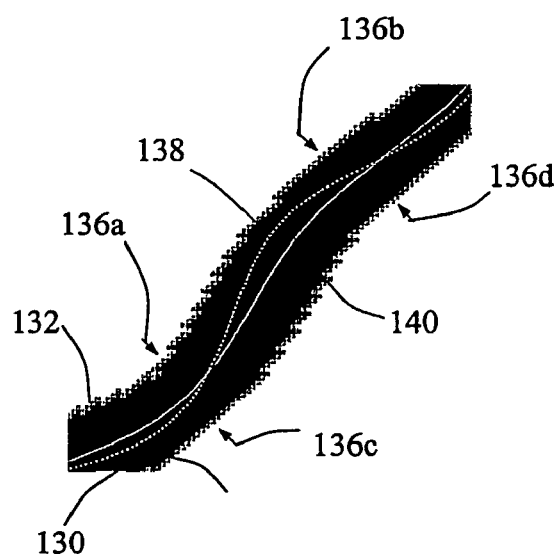
FIGURE 13A          FIGURE 13B

  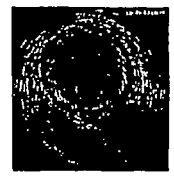 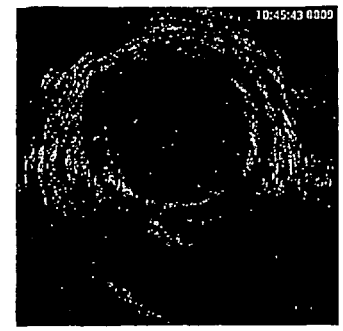
FIGURE14A  FIGURE 14B  FIGURE 14C  FIGURE14D
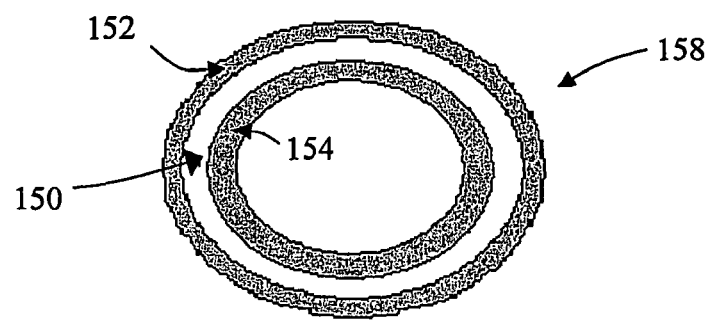
FIGURE 15

US 7,925,064 B2

AUTOMATIC MULTI-DIMENSIONAL INTRAVASCULAR ULTRASOUND IMAGE SEGMENTATION METHOD

This application is a national phase application under 35 U.S.C. §371 of International Application No. PCT/CA2004/001970 filed 15 Nov. 2004, which claims priority to Canadian Patent Application No. 2,449,080 filed 13 Nov. 2003, the contents of which are incorporated herein by reference in their entirety.

FIELD OF THE INVENTION

The present invention generally relates to image segmentation. More specifically but not exclusively, the present invention is concerned with an intravascular ultrasound image segmentation technique for characterizing blood vessel vascular layers from intravascular ultrasound image sequences.

BACKGROUND OF THE INVENTION

Over the past few years, intravascular ultrasound (IVUS) technology has become very useful for studying atherosclerotic disease. IVUS is a medical imaging technique that produces cross-sectional images as a catheter is pulled-back inside a blood vessel. These images show the lumen but also the layered structure of the vascular wall. IVUS provides quantitative assessment of the vascular wall, information about the nature of atherosclerotic lesions as well as the plaque shape and size such that in clinic, IVUS was rapidly recognized as a valuable tool in diagnosis and in pre-intervention analysis of atherosclerosis.

The ability to characterize the vascular wall was initially demonstrated in 1989 by Gussenhoven et al., in "Arterial wall characteristics determined by intravascular ultrasound imaging: An in vitro study" (*J. Am. Coll. Cardiol.*, vol. 14, no. 4, pp. 947-952, 1989). Also, studies of the mid-90s by Mintz et al., in "Atherosclerosis in angiographically 'normal' coronary artery reference segments: An intravascular ultrasound study with clinical correlations" (*J. Am. Coll. Cardiol.*, vol. 25, no. 7, pp. 1479-1485, 1995), showed, based on IVUS, that 40% of angiographically normal vessel were in fact atherosclerotic.

By using IVUS, it was also demonstrated by Colombo et al., in "Intracoronary stenting without anticoagulation accomplished with intravascular ultrasound guidance" (*Circulation*, vol. 91, pp. 1676-1688, 1995) that conventional stent implantation resulted in incomplete apposition and expansion causing thrombosis, which had the result of changing the clinical practice.

IVUS is also expected to play an important role in atherosclerosis research. For example, as demonstrated by Nissen et al., in "Application of intravascular ultrasound to characterize coronary artery disease and assess the progression or regression of atherosclerosis" (*Am. J. Cardiol.*, vol. 89, pp. 24B-31B, 2002), IVUS helps to achieve precise evaluation of the disease in new progression-regression therapies. Experts also generally agree that IVUS imaging adds precious complementary information to angiography which only shows a projection of the lumen, as taught by Nissen et al., in "Intravascular ultrasound: Novel pathophysiological insights and current clinical applications" (*Circulation*, vol. 103, pp. 604-616, 2001).

Over the last few years, new signal processing strategies were applied to IVUS signals for extracting information on the elastic properties of the vascular wall. For example, a new imaging technique named "intravascular or endovascular ultrasound elastography" was proposed by de Korte et al., in "Intravascular elasticity imaging using ultrasound—Feasibility studies in phantoms" (*Ultrasound Med. Bio.*, vol. 23, pp. 735-746, 1997). Recently, Brusseau et al. in "Fully automatic luminal contour segmentation in intracoronary ultrasound imaging—A statistical approach" (*IEEE Trans. Med. Imag.*, vol. 23, pp. 554-566, 2004) suggested to use a pre-segmentation of the structures of the vascular wall identified from IVUS images to help implementing elastography algorithms. This constitutes another important domain of application of IVUS multi-dimensional image segmentation.

The tomographic nature of IVUS makes 3D reconstruction of the vessel wall possible. Furthermore, 2D and 3D quantitative measurements of atherosclerotic disease such as plaque volume, intima-media thickness, vascular remodeling, and lumen area stenosis can be retrieved from IVUS data as disclosed by Mintz et al., in "American college of cardiology clinical expert consensus document on standards for acquisition, measurement and reporting of intravascular ultrasound studies (IVUS)" (*J. Am. Coll. Cardiol*, vol. 37, no. 5, pp. 1478-1492, 2001).

However, a typical IVUS acquisition generally contains several hundreds of images, which has the effect of making analysis of the data a long and fastidious task that is further subject to an important variability between intra-observers and inter-observers when non-automatic methods are used. These aspects generate important constraints against the clinical use of IVUS. Other constraints related to the use of IVUS include poor quality image due to speckle noise, imaging artifacts, and shadowing of parts of the vessel wall by calcifications.

So far, a number of segmentation techniques have been developed for IVUS data analysis and were introduced to overcome the hereinabove discussed drawbacks. Generally speaking, a portion of these techniques are based on local properties of image pixels, namely with the gradient-based active surfaces as introduced by Klingensmith et al., in "Evaluation of three-dimensional segmentation algorithms for the identification of luminal and medial-adventitial borders in intravascular ultrasound images" (*IEEE Trans. Med. Imag.*, vol. 19, no. 10, pp. 996-1011, 2000) and the pixel intensity combined to gradient active contours as introduced by Kovalski et al., in "Three-dimensional automatic quantitative analysis of intravascular ultrasound images" (*Ultrasound Med. Biol.*, vol. 26, no. 4, pp. 527-537, 2000).

Graph search was also investigated using local pixel features, for instance, with Sobel-like edge operator as disclosed by Zhang et al., in "Tissue characterization in intravascular ultrasound images" (*IEEE Trans. Med. Imag.*, vol. 17, no. 6, pp. 889-899, 1998) and with gradient associated to line patterns correlation as demonstrated by Von Birgelen et al., in "Morphometric analysis in three-dimensional intracoronary ultrasound: An in vitro and in vivo study using a novel system for the contour detection of lumen and plaque" (*Am. Heart J.*, vol. 132, no. 2, pp. 516-527, 1996).

The other portion of the IVUS segmentation work was based on more global or region information. For instance, texture-based morphological processing was considered as disclosed by Mojsilovic et al., in "Automatic segmentation of intravascular ultrasound images: A texture-based approach" (*Ann. Biomed. Eng.*, vol. 25, no. 6, pp. 1059-1071, 1997). Gray level variances were then used for the optimization of a maximum a posteriori (MAP) estimator modeling ultrasound speckle and contour geometry as demonstrated by Haas et al., in "Segmentation of 3D intravascular ultrasonic images based on a random field model" (*Ultrasound Med. Biol.*, vol. 26, no. 2, pp. 297-306, 2000).

In addition, some studies defining only the lumen boundary and not using the full IVUS potential can be found in the literature. Still, in 2001, the clinical expert consensus from the American College of Cardiology in the hereinabove cited document by Mintz et al. reported that no IVUS edge detection method had found widespread acceptance by clinicians.

Recently, graph search was revisited using other edge filters, as disclosed by Koning et al., in "Advanced contour detection for three-dimensional intracoronary ultrasound: A validation—in vitro and in vivo" (*Int. J. Cardiac Imag.*, vol. 18, pp. 235-248, 2002).

Other recent models and methods were proposed, such as elliptical template fitting as demonstrated by Weichert et al., in "Virtual 3D IVUS model for intravascular brachytherapy planning: 3D segmentation, reconstruction, and visualization of coronary artery architecture and orientation" (*Med. Phys.*, vol. 30, no. 9, pp. 2530-2536, 2003) and multiagent segmentation by Bovenkamp et al., in "Multiagent IVUS image interpretation" (*SPIE Proceedings: Medical Imaging 2003: Image Processing*, vol. 5032, San-Diego, USA, 2003, pp. 619-630). However, these new models were again using local pixel or edge information and they were not taking advantage of the statistical information of IVUS data (speckle texture).

Since image pixels in IVUS have pixel gray values generally distributed according to a Rayleigh probability density function (PDF) in B-mode (brightness modulation) imaging of uniform scattering tissues, as demonstrated by Wagner et al., in "Statistics of speckle in ultrasound B-scans" (*IEEE Trans. Son. Ultrason.*, vol. 30, no. 3, pp. 156-163, 1983), it is believed that PDF features can be of value for IVUS segmentation. This information is hypothetically more suitable for IVUS image analysis, especially when contrast is low between layers of the vascular wall. In addition, because the IVUS radio-frequency (RF) mode generally provides a better spatial resolution than B-mode imaging, it is also expected that the Gaussian PDF of RF images can be exploited for image segmentation.

Since the atherosclerotic plaque structure on the vascular wall can have an irregular and complex shape that is rarely elliptical, a fast marching method as disclosed by Sethian in "*Level Set Methods and Fast Marching Methods: Evolving Interfaces in Computational Geometry, Fluids Mechanics, Computer Vision and Materials Science*" (2nd ed. Cambridge, UK: Cambridge University press, 1999) and by Osher et al., in "Fronts propagating with curvature-dependent speed: Algorithms based on hamilton-jacobi formulations" (*J. Comput. Phys.*, vol. 79, pp. 1249, 1988), can be used to handle topological changes and contour irregularities generated by IVUS images. Further, the fact that a fast marching method propagates interfaces in the direction of the boundaries through an exhaustive analysis of the propagation region has the effect of decreasing the variability of segmentation results.

SUMMARY OF THE INVENTION

More specifically, in accordance with the present invention, there is provided an image segmentation method for estimating boundaries of layers in a multi-layer body, the method including providing image data of the multi-layer body, the image data representing a plurality of image elements. The method further includes determining a plurality of initial interfaces corresponding to regions of the image data to segment, and concurrently propagating the initial interfaces corresponding to the regions to segment and thereby estimating the boundaries of the layers of the multi-layer body. Propagating the initial interfaces including using a fast marching model based on a probability function describing at least one characteristic of the image elements.

There is furthermore provided an image segmentation method for estimating boundaries of layers in a multi-layer body, the method including providing image data of the multi-layer body, the image data representing a plurality of image elements. The method further includes determining a plurality of initial interfaces corresponding to regions of the image data to segment, and concurrently propagating the initial interfaces corresponding to the regions to segment the regions and estimate the boundaries of the layers of the multi-layer body. Propagating the initial interfaces includes using a fast marching model based on a gradient function describing at least one characteristic of the image elements.

There is furthermore provided an image segmentation method for estimating boundaries of layers in a pulsating multi-layer blood vessel, the method including: providing IVUS image data of the pulsating multi-layer blood vessel, determining initial interfaces corresponding to the regions of the IVUS image data to segment, dividing wall pulsations of the IVUS image data into a discrete number of phases with adjustable pulsation phase labels, assigning the pulsation phase labels to 2D IVUS frames of the IVUS image data, dividing the IVUS image data according to the phases and propagating the initial interfaces according to a fast marching model by simultaneously estimating a mixture of probability density functions in the IVUS image data for each of the regions to segment and according to each of the phases.

There is furthermore provided an image segmentation method for estimating boundaries of layers in a multi-layer body, the method including: providing image data of the multi-layer body, the image data representing a plurality of image elements. The method further includes determining initial interfaces corresponding to the regions of the image data to segment and propagating the initial interfaces according to a fast marching model. Propagating the initial interfaces includes, for each region to segment, simultaneously estimating a speed function for the propagation of the initial interfaces based on a probability function describing at least one characteristic of the image elements, and mapping a time function of the propagating initial interfaces.

There is furthermore provided a data acquisition system for segmenting images by estimating boundaries of layers in a multi-layer body, including: a catheter including a transducer for providing image data representing a plurality or image elements and a data acquisition tool including: a digitizer in communication with the transducer for digitizing the image data, a memory for receiving and storing the digitized image data, a calculator for estimating, for each of the layers, probability functions describing at least one characteristic of the image elements, a processor in communication with the memory and the calculator for simultaneously estimating the boundaries of the layers of the digitized image data by using a fast marching model based on the estimated probability functions.

The foregoing and other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

In the appended drawings:

FIG. 7a is a cross-sectional view of a simulated blood vessel reconstructed according to a segmented 2D IVUS frame;

FIG. 7b is a 2D IVUS frame view of the simulated blood vessel of FIG. 7a and generated by the method shown in FIG. 6;

FIG. 7c is a 2D IVUS frame view showing the segmentation results on the 2D IVUS frame view of FIG. 7b, with the boundaries detected by the 3D fast marching method based on probability density functions;

FIG. 7d is a 2D IVUS frame view showing the segmentation results on the 2D IVUS frame view of FIG. 7b, with the boundaries detected by the 3D gradient fast marching method;

FIG. 8a is another cross-sectional view of a simulated blood vessel reconstructed according to a segmented 2D IVUS frame;

FIG. 8b is a 2D IVUS frame view of the simulated blood vessel of FIG. 8a and generated by the method shown in FIG. 6;

FIG. 8c is a 2D IVUS frame view showing the segmentation results on the 2D IVUS frame view of FIG. 8b, with the boundaries detected by the 3D fast marching method based on probability density functions;

FIG. 8d is a 2D IVUS frame view showing the segmentation results on the 2D IVUS frame view of FIG. 8b, with the boundaries detected by the 3D gradient fast marching method;

FIG. 9a is a 2D IVUS frame view similar to the one shown in FIG. 1;

FIG. 9b is a 2D IVUS frame view showing the segmentation results on the 2D IVUS frame view of FIG. 9a, with the boundaries detected by the 3D fast marching method based on probability density functions;

FIG. 9c is a 2D IVUS frame view showing the segmentation results on the 2D IVUS frame view of FIG. 9a, with the boundaries detected by the 3D gradient fast marching method;

FIG. 10a is a 2D IVUS frame view similar to the one shown in FIG. 1;

FIG. 10b is a 2D IVUS frame view showing the segmentation results on the 2D IVUS frame view of FIG. 10a, with the boundaries detected by the 3D fast marching method based on probability density functions;

FIG. 10c is a 2D IVUS frame view showing the segmentation results on the 2D IVUS frame view of FIG. 10a, with the boundaries detected by the 3D gradient fast marching method;

FIG. 11 is a longitudinal view showing a volumic reconstruction of the vessel layers detected according to the fast-marching method based on probability density functions;

FIG. 12a is a 2D IVUS frame view representing the various layers of a blood vessel on simulated RF image data;

FIG. 12b is a 2D IVUS frame view showing the segmentation results on the RF image data of FIG. 12a, with the boundaries detected by the 3D fast-marching method based on probability density functions;

FIG. 13a is a detailed schematic view showing a first example of propagation area for detecting a layer boundary using the fast marching method;

FIG. 13b is a detailed schematic view showing another example of propagation area for detecting a layer boundary using the fast marching method;

FIG. 14a is a 2D IVUS frame view which is undersampled with respect to a typical 2D IVUS frame and which may be used according to a second illustrative embodiment of the present invention;

FIG. 14b is another 2D IVUS frame view which is undersampled with respect to a typical 2D IVUS frame but with a higher resolution than the 2D IVUS view shown in FIG. 14a;

FIG. 14c is another 2D IVUS frame view which is undersampled with respect to a typical 2D IVUS frame but with a higher resolution than the 2D IVUS view shown in FIG. 14b;

FIG. 14d is a typical 2D IVUS frame view with a higher resolution than the 2D IVUS views shown in FIG. 14a to 14c;

FIG. 15 is a detailed schematic view showing template regions of a vessel for detecting layer boundaries in a method according to a third illustrative embodiment of the invention;

DETAILED DESCRIPTION OF THE ILLUSTRATIVE EMBODIMENTS

The non-restrictive illustrative embodiments of the present invention relate to a method and device for concurrently estimating boundaries between the plurality of layers of a blood vessel from IVUS image data. The method and device involve a segmentation of the IVUS image data by propagating interfaces in each layer to be estimated from initial interfaces that are generated from the IVUS image data. The technique for estimating the boundaries of the various layers uses a fast marching method based on probability functions, such as for example a probability density function (PDF) or gradient function to estimate the distribution color map of images, such as for example to estimate the gray levels or the multi-colored levels in images.

The following description is organized as follows. First of all, a PDF estimation technique for the different vessel layers will be presented. Then, an IVUS 3D fast marching method based on the estimated PDFs and based on the gray level gradient will be explained and followed by an initializing technique. Finally, segmentation results on experimental B-mode data, simulated B-mode and simulated RF data and will be reported and discussed.

Figure 1:
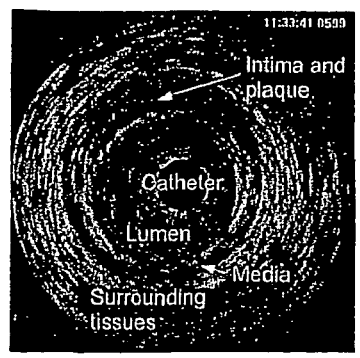
FIG. 1 is a 2D IVUS frame view representing the various layers of a blood vessel in image data which is used in a segmentation method for detecting layer boundaries according to an illustrative embodiment of the present invention.
Figure 2:
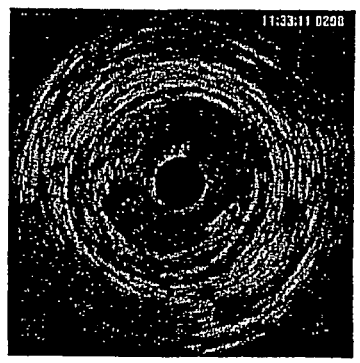
FIG. 2 is another 2D IVUS frame view representing one irregularly shaped layer of the blood vessel shown in FIG. 1.

IVUS images are generally provided from an ultrasound transducer at the tip of a catheter that is pulled back inside a blood vessel and produces a plurality of IVUS 2D frames. A typical IVUS 2D frame is illustrated in FIG. 1. As illustrated, the 2D frame of FIG. 1 shows the catheter and some layers of the blood vessel such as, for example, the lumen, the intima and plaque, the media and the surrounding tissues. FIG. 2 illustrates how the boundary of the lumen may be irregularly shaped.

The IVUS 2D frames are ultrasonic images made from a plurality of pixels generally colored with various shades of gray. In B-mode (brightness modulation) or RF-mode (radio-frequency) imaging, such as for example in IVUS data, a Rayleigh or a Gaussian probability density function (PDF) can be used, respectively, to model the color map distribution of the ultrasonic speckle pattern in a uniform scattering tissue. When more than one layer of tissue is present, the color map distribution of a whole IVUS image data can then be modeled by a mixture of Rayleigh or Gaussian PDFs, depending on the mode selected on the instrument.

The illustrative embodiment that follows generally considers IVUS B-mode imaging, but one ordinary skilled in the art will easily understand that similar equations can be provided for Gaussian PDFs if the RF-mode is considered. For more details, see Hastie et al., in "The elements of statistical learning. Data mining, inference and prediction" (New York, USA: Spinger, pp. 236-242, 2001).

In this first illustrative embodiment, a Rayleigh probability density function (PDF) $p_X(x)$ models the gray level color map distribution by using a parameter $a^2$, where x is the gray level taking values situated, for example, in the range [1, ..., 256]. In this particular example, the Rayleigh probability density function (PDF) is given by equation 1:

$$p_x(x; a^2) = \frac{x}{a^2} \exp\left(-\frac{x}{2a^2}\right) \quad (1)$$

with $x, a^2 > 0$, and the variance $\sigma^2 = a^2(4-\pi)/2$.

IVUS data are modeled by a mixture of M Rayleigh PDFs (corresponding to M different layers of the blood vessel) with parameters $\Theta = \{(\omega_j, a_j^2)\}_{j=1}^M$ where $\omega_j$ is the proportion of the $j^{th}$ component of the mixture of the M Rayleigh PDFs, so that $\Sigma_{j=1}^M \omega_j = 1$. The global data PDF mixture then becomes:

$$p_{X|\Theta}(x|\Theta) = \sum_{j=1}^M \omega_j p(x|a_j^2) \quad (2)$$

Figure 3:
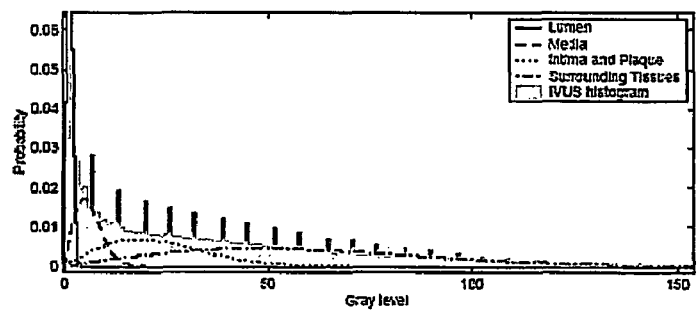
FIG. 3 is a chart view showing the gray levels present in IVUS image data and the mixture of the probability density functions detected per layer.

To describe the PDF mixture for the global IVUS data, the parameters $(\omega_j, a_j^2)$ of each PDF composing the mixture need to be estimated. In IVUS data, the occurring probability of the gray level values x, or observed data, can generally be measured by computing the image histogram, as shown in FIG. 3, but the blood vessel layer to which each pixel of an IVUS image belongs is generally unknown or hidden for images that are not already segmented.

The Expectation-Maximization algorithm (EM) is an iterative computation technique of maximum likelihood estimates for incomplete data, as presented by Dempster et al., in "Maximum likelihood from incomplete data via the EM algorithm" (J. Roy. Stat Soc. B, vol. 39, no. 1, pp. 1-38, 1977), which can be used to provide the unknown parameters or hidden information of the probability density functions (PDFs). Because the IVUS data are incomplete in terms of maximum likelihood estimation, the EM algorithm can be applied to evaluate the missing or hidden mixture parameters of the Rayleigh or Gaussian PDFs.

The EM algorithm therefore helps to describe the global data PDF mixture because $\hat{\Theta}$, a mixture parameter maximizing the likelihood of $p(x|\Theta)$, cannot be solved analytically. A hidden variable Y representative of the tissue class (vascular layer to which the pixel belongs) and taking values situated in the range [1, ..., M], must be introduced at this point. The log-likelihood of the joint distribution of $(X,Y) = \{(x_i, y_i)\}_{i=1}^N$, where N represents the size of the IVUS data, is:

$$\log(p_{X,Y|\Theta}(x, y|\Theta)) = \sum_{i=1}^N \log p(y_i) p(x_i|y_i, \Theta) \quad (3)$$

The first step of the EM algorithm is called the Expectation Step which calculates the cost function $Q(\Theta, \Theta') = E_Y[\log(P(X,Y|\Theta))|X, \Theta']$, the expected value of the log-likelihood of $(X,Y)$, the joint distribution, given the observed data X and $\Theta' = \{(\omega'_j, a_j^{2'})\}_{j=1}^M$, a previous estimate of the PDF mixture parameters.

The next step is to determine a new estimate $\hat{\Theta}$ of the PDF mixture parameters by maximizing $Q(\Theta, \Theta')$ with respect to parameters $\Theta$; this operation can now be performed analytically.

The detailed PDF parameter estimation procedure via the EM algorithm is therefore:

Initialize $\Theta'$, the previous estimate of PDF mixture parameters.

Expectation Step:
Evaluate the cost function:

$$Q(\Theta, \Theta') = E_Y[\log(P(X, Y|\Theta))|X, \Theta'] \quad (4)$$

$$= \sum_{j=1}^M \sum_{i=1}^N \log(\omega_j p(x_i|a_j^2) p(y_i = j|x_i, \Theta')) \quad (5)$$

Calculate $p(y_i = j|x_i, \Theta') = \dfrac{\omega'_j p(x_i|a_j^{2'})}{\sum_{k=1}^M \omega'_k p_k(x_i|a_k^{2'})},$ according to Bayes rule, and using the previous parameter estimate Θ' and Equation 1.

Maximization Step:

Calculate $\hat{\Theta}$, the new estimate of the PDF mixture parameters:

$$\hat{\omega}_j = \text{argmax}_{\omega_j}\left(Q(\Theta, \Theta') + \lambda\left(1 - \sum_{j=1}^{M}\omega_j\right)\right) \quad (6)$$

$$= \frac{1}{N}\sum_{i=1}^{N} p(y_i = j \mid x_i, \Theta')$$

where λ=N is a Lagrangian making the sum of the $\omega_j$ equal to 1.

$$\hat{a}_j^2 = \text{argmax}_{a_j^2} Q(\Theta, \Theta') \quad (7)$$

$$\hat{a}_j^2 = \frac{\sum_{i=1}^{N} p(y_i = j \mid x_i, \Theta') x_i^2}{2\sum_{i=1}^{N} p(y_i = j \mid x_i, \Theta')}.$$

If $\hat{\Theta} \neq \Theta'$, update previous estimate $\Theta' = \hat{\Theta}$, and repeat the Expectation and Maximization steps.

In summary, the EM algorithm maximizes the likelihood of the joint distribution of the observed and hidden data by estimating the posterior distribution with $p_{Y|X,\Theta'}(y|x,\Theta')$. An interesting property of the EM algorithm is that it is guaranteed that the likelihood of the observed data X increases at each iteration.

For computation efficiency, the EM algorithm is generally applied to a randomly drawn subset of the observed data X, which are, in this case, a portion of the pixels from the whole IVUS data. For instance, the subset size may be about 400 000 pixels when a complete IVUS pullback generally contains over 80 000 000 pixels.

EM algorithms are otherwise well known to those of ordinary skill in the art and, accordingly, will not be further described in the present specification.

The estimated gray level PDFs of the blood vessel layers can then be used to establish a segmentation model in the fast marching framework. The fast marching method is derived from the level-set model disclosed by Sethian in "*Level Set Methods and Fast Marching Methods: Evolving Interfaces in Computational Geometry, Fluids Mechanics, Computer Vision and Materials Science*" (2nd ed. Cambridge, UK: Cambridge University press, 1999) and by Osher et al., in "Fronts propagating with curvature-dependent speed: Algorithms based on hamilton-jacobi formulations" (*J. Comput. Phys.*, vol. 79, pp. 1249, 1988). The fast marching method helps to follow interface propagation.

In the level-set model approach, an initial interface is defined as the zero level of a function ϕ of a higher dimension than the interface. The value ϕ(x) of a point x=(x1, x2, . . . , $x_n) \in \Re^n$ is the distance between that point and the initial interface. The function ϕ moves in its normal direction according to a speed function F. The evolution of function ϕ is given by the following Equation 8 with initial interface ϕ(x,t=0).

$$\frac{\partial \phi}{\partial t} + F|\nabla \phi| = 0. \quad (8)$$

The level-set model is applicable to image segmentation by interpreting image boundaries as the final position of the propagating interface, as disclosed by Sethian in "*Level Set Methods and Fast Marching Methods: Evolving Interfaces in Computational Geometry, Fluids Mechanics, Computer Vision and Materials Science*" (2nd ed. Cambridge, UK: Cambridge University press, 1999) and by R. Malladi et al., in "Shape modeling with front propagation: A level set approach" (*IEEE Trans. Pattern Anal. Machine Intell.*, vol. 17, no. 2, pp. 158-175, 1995).

To achieve this, the speed function F is defined in terms of image or shape features and should become close to zero when the propagating interface meets with image boundaries. Since the speed value is near zero, the propagating interface stops on the image boundary, which generally ends the segmentation process.

Fast marching is a particular case of the level-set model. It consists of an interface evolving under a unidirectional speed function. In this case; for a positive speed function, the propagating interface must be inside the region to segment (or outside for a negative speed function), because the propagating interface does not explore the region located inside the initial interface.

In the fast marching formulation, the evolution of the propagating interface is expressed in terms of the arrival time T(x) of the interface at point (x). The function T satisfies the following Equation 9, stating that the arrival time difference between two adjacent pixels increases as the velocity of the interface decreases.

$$|\nabla T|F = 1. \quad (9)$$

The propagation of the interface is done via the construction of the arrival time function T(x). The construction algorithm, as disclosed by Sethian in "A fast marching level set method for monotonically advancing fronts." (*Proceedings of the National Academy of Sciences of the United States of America*, vol. 93, pp. 1591-1595, 1996), selects the interface point x having the smallest arrival time and calculates the arrival times of its neighbors. This is repeated until the interface has propagated across the whole image or until the propagating interface is considered stationary (when the time gradient is sufficiently high).

The level-set and fast marching equations are independent of the interface dimension. On a discrete 3D grid, neighbors' arrival times are updated by solving the following approximation of Equation 9:

$$\frac{1}{F_{i,j,k}^2} = \max(D_{i,j,k}^{-x}T, -D_{i,j,k}^{+x}T, 0)^2 + \quad (10)$$
$$\max(D_{i,j,k}^{-y}T, -D_{i,j,k}^{+y}T, 0)^2 + \max(D_{i,j,k}^{-z}T, -D_{i,j,k}^{+z}T, 0)^2$$

For the x dimension, $$D_{i,j,k}^{\pm x}T = \pm(T_{i\pm1,j,k} - T_{i,j,k})/\Delta$$

where Δ is the grid element size and (i,j,k) is the 3D position of the point having its arrival time calculated. Similar definitions apply for $D_{i,j,k}^{\pm y}T$ and $D_{i,j,k}^{\pm z}T$, in the y and z dimensions.

As stated hereinabove, since multiple contours (lumen, intima and media) must be identified on the IVUS data, image segmentation is simultaneously done via a multiple interface extension of the fast marching method as disclosed by Sifakis et al., in "Bayesian level sets for image segmentation" (*J. Vis. Commun. Image R.*, vol. 13, pp. 44-64, 2002). A speed function is then defined for each propagating interface and the T map is built by selecting the point with the smallest arrival time value from all propagating interfaces.

Therefore, the fast marching method with multiple propagating interfaces enables simultaneous segmentation of different layers of the blood vessel. The multiple interfaces directly depict the layered structure of the blood vessel and provide that the boundaries do not overlap.

In the PDF-based fast marching method, each interface associated to a vessel layer evolves at a velocity defined in terms of the PDF $P_{m \in L}$ of the corresponding anatomical structure. The propagation speed of the interface m∈L, where L is the set $1, 2, \ldots, N_L$ of the $N_L$ evolving interfaces, is given by Equation 11.

$$F_m(i, j, k) = \left(1 + \frac{1}{N_v} \sum_{s \in v} \frac{\log P_m(I_s)}{\frac{1}{N_L - 1} \sum_{l \neq m, l \in L} \log P_l(I_s)}\right)^{-1}. \quad (11)$$

$I_s$ is the gray level value of pixel s at position (i,j,k) in image I, $P_m(I_s)$ and $P_l(I_s)$ are the measured occurring probabilities of pixel $I_s$ in region m and l, respectively. Because the occurring probability is more significant for a region than for a single pixel, the speed function is calculated over a certain number $N_v$ of neighbors, which are pixels located around position (i,j,k), such as for example, the 26-connected pixels around position (i,j,k). According to Equation 11, the m interface velocities will usually be positive and take higher values when inside a region having a grayscale distribution close to $P_m$.

As the propagating interfaces approach the boundaries of the blood vessel layers, neighbors start to be distributed under other components of the PDFs as stated hereinabove, which has the effect of generally increasing $P_l(I_s)$ and decreasing $P_m(I_s)$ and therefore, decreasing the interface speed. The velocity function of Equation 11 has a general form that may be used with any types of PDF and provides neighborhood averaging.

When used for multiple propagating interfaces, the fast marching segmentation method ends when all adjacent propagating interfaces meet with their respective boundaries. Propagating interfaces thus evolve until the arrival time T map is completely built.

Since the gray level gradient is a widely accepted image feature, comparisons can be made between the hereinabove disclosed PDF implementation of the fast marching segmentation and a gray level gradient implementation of the fast marching segmentation. In the latter case, the speed function is given by:

$$F(i, j, k) = \frac{1}{1 + |\nabla G_\sigma * I(i, j, k)|} \quad (12)$$

where $G_\sigma$ is a Gaussian smoothing filter of standard deviation σ. The speed function of Equation 12 generally propagates interfaces faster on low gradient regions.

As stated hereinabove, the fast marching segmentation method generally requires that the initial interface is located inside the region to segment. This requirement can be achieved with an initialization procedure, in which initialization contours are manually traced with respect to data extracted along longitudinal planes of the IVUS data. It can also be automatically performed by considering a priori information on the whole IVUS data set, as will be further described hereinafter.

Generally speaking, the step of selecting data along longitudinal planes within the IVUS data is used, instead of using data from a single 2D IVUS frame, since longitudinal planes are able to provide information about the whole series of data along the length of the blood vessel. Further, the number of manually or automatically traced initialization contours on the longitudinal plane is independent of the number of IVUS 2D frames.

Initialization contours may be drawn from different numbers of longitudinal planes along the blood vessel. As an example, 3 longitudinal planes taken at equally spaced angles over 360 degrees may be selected to cut the IVUS data volume. The initialization contours provide reference points for generating the set of initial interfaces on each IVUS 2D frame, for each of the layers to be estimated. This is generally accomplished by attributing respective reference points to the IVUS 2D frame corresponding to each initialization contour points.

Figure 4:
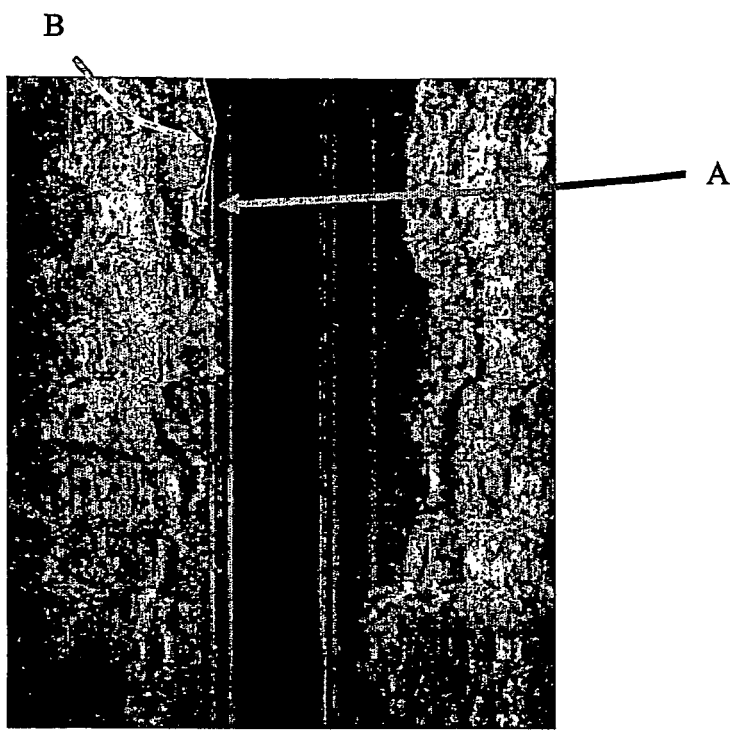
FIG. 4 is a longitudinal view generated from IVUS image data showing an operation of a method for detecting the layer boundaries.
Figure 5:
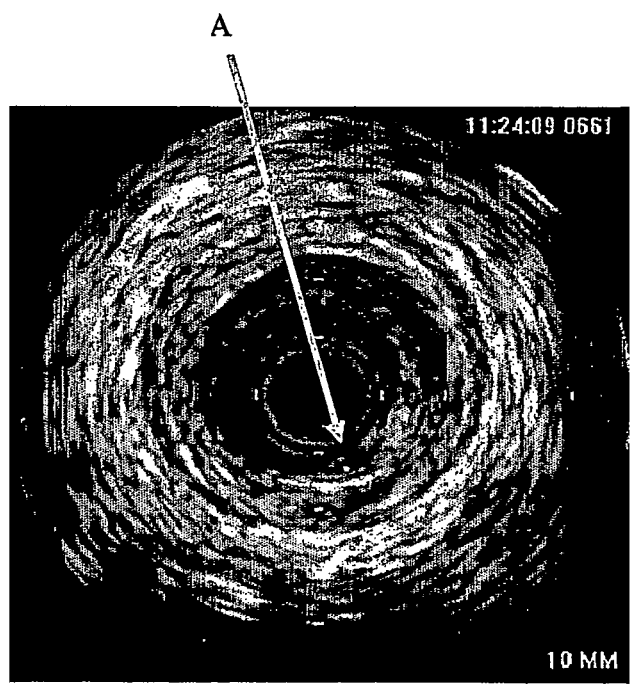
FIG. 5 is a 2D IVUS frame view intersecting the longitudinal view of FIG. 4 at point A.
Figure 18:
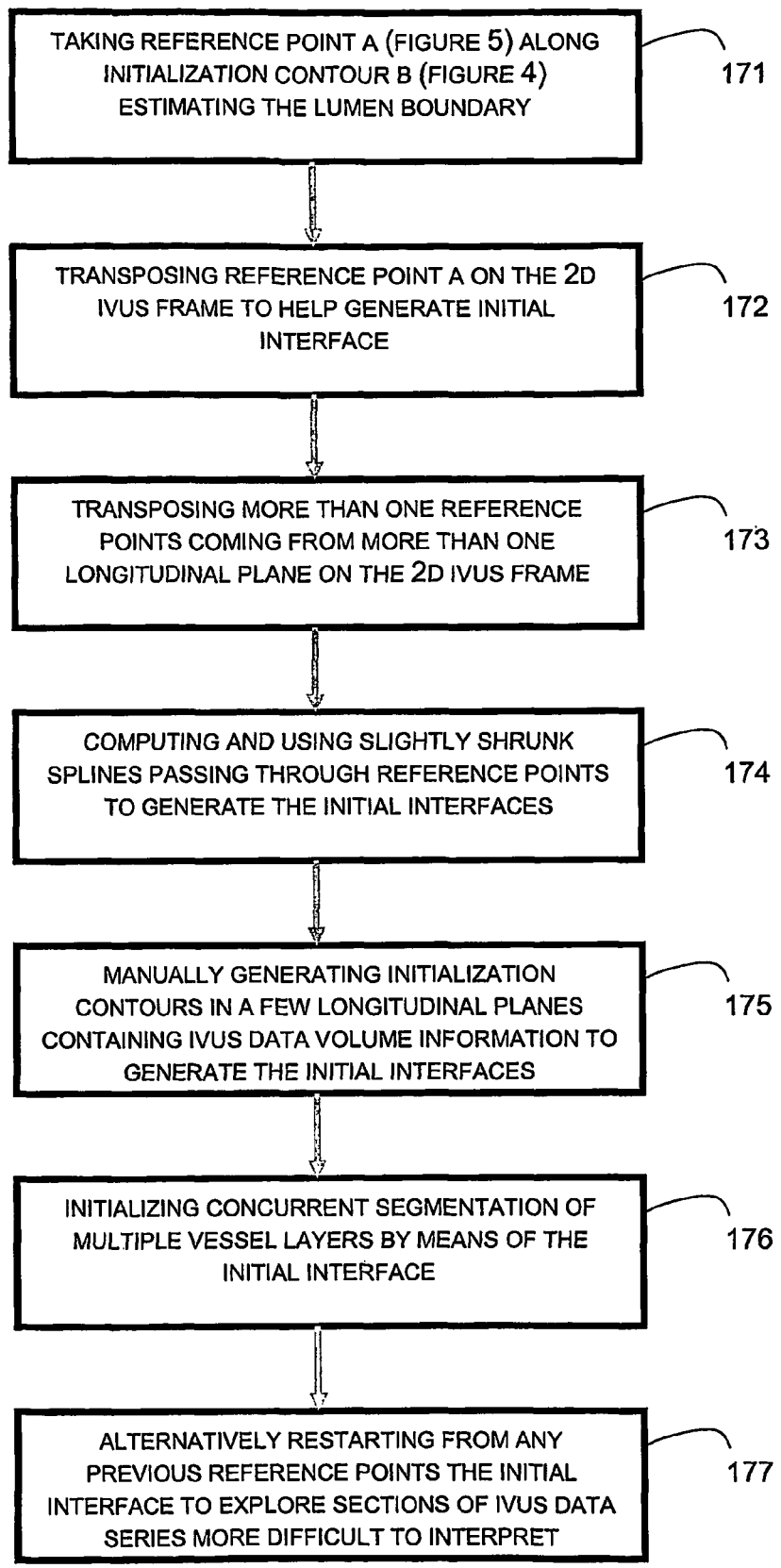
FIG. 18 is a flowchart representing a method for determining the initialization contours according to the first illustrative embodiment of the present invention.

In the illustrative embodiment of FIGS. 4 and 5, a reference point A is taken along to one initialization contour B estimating the lumen boundary on the longitudinal plane shown in FIG. 4 (Operation 171 of FIG. 18). For instance, the reference point A of FIG. 4 is transposed on the IVUS 2D frame of FIG. 5 to help generate the initial interface of the lumen on the IVUS 2D frame (Operation 172 of FIG. 18). More than one reference points generally coming from more than one longitudinal plane are then transposed on the IVUS 2D frame (Operation 173 of FIG. 18). This initialization step is generally done for each boundary layer of the blood vessel which needs to be estimated.

For each IVUS 2D frame, slightly shrunk splines passing through these reference points are computed and used to generate the initial interfaces (Operation 174 of FIG. 18). Therefore, using this procedure, only a few longitudinal planes containing IVUS data volume information are required to manually generate the initialization contours in the longitudinal planes and thereby to generate the initial interfaces (Operation 175 of FIG. 18) required to initialize the concurrent segmentation of multiple vessel layers (Operation 176 of FIG. 18), over several hundreds of images which is a typical number for a typical IVUS data.

The initial longitudinal contours can also alternatively be restarted from any previous reference points (Operation 177 of FIG. 18). In this manner, the user can explore, on-line and easily, sections of an IVUS data that were more difficult to interpret on longitudinal planes.

Experimental Testings

Figure 19:
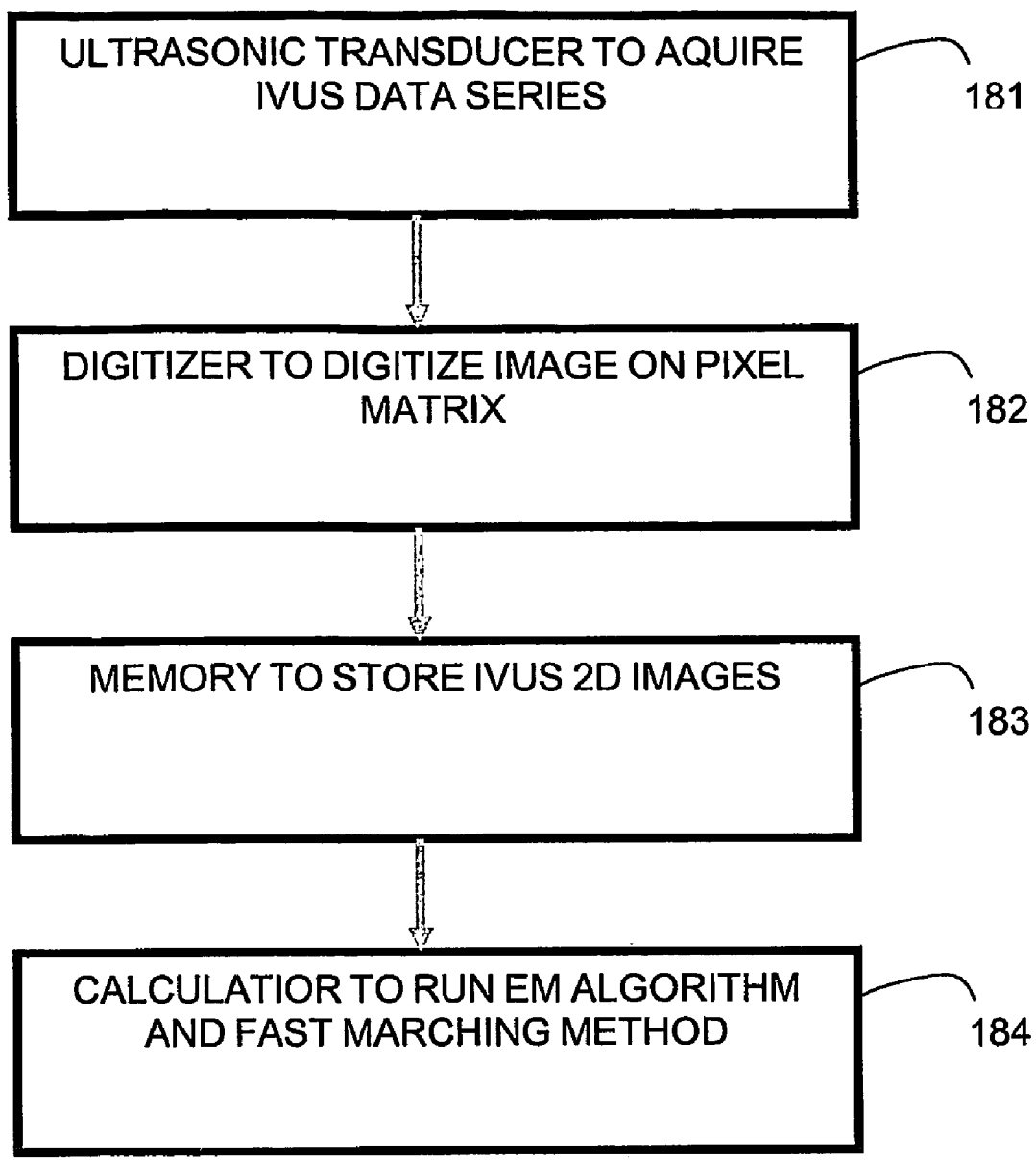
FIG. 19 is a block diagram representing an in-vivo IVUS data acquisition and processing device according to the first illustrative embodiment of the present invention.

Experimental testings of the hereinabove proposed non-restrictive illustrative method of FIG. 18 were conducted on a total of 8 in-vivo IVUS pullbacks (600 frames/IVUS data) from diseased superficial femoral arteries. These experimental testings were performed on 6 different patients before undergoing balloon angioplasty. B-mode IVUS data were acquired with a data acquisition system, such as for example a Jomed equipment (In-vision gold, Helsingborg, Sweden), using a 20 MHz ultrasonic transducer (181 in FIG. 19). IVUS 2D B-mode images of size 10×10 mm were digitized (digitizer 182 in FIG. 19) on 384×384 pixel matrices and stored in a memory (183 in FIG. 19) using the DICOM standard. The acquisition was done at a 10 images/sec frame rate and the catheter pullback velocity was set to 1 mm/sec generating 0.1 mm thick 2D slices. Acquisition parameters were set by a clinician to optimize image quality; more specifically, the gain varied from 46 to 54 and the grayscale look-up table was set to 5. Image acquisition was not ECG-gated.

To evaluate the robustness of the PDF mixture parameter estimation of $\omega_j$ and $a_j^2$, the hereinabove described EM algorithm was run 10 times in a calculator (184 in FIG. 19) for one IVUS catheter pullback, with different subsets of pixels at each run of the algorithm. Average PDF mixture parameters and standard deviations were calculated for the detected Rayleigh PDFs. Since pixel subsets were from the same IVUS data, PDF mixture parameters were expected to generally converge toward the same values.

Once this robustness validation was completed, the EM algorithm was applied at the beginning of each segmentation, because PDF mixture parameters are specific to each IVUS data, as gain and other parameter settings are different between each IVUS data, and as echogenicity of each layer is variable from one patient to the other. The detected PDF mixtures were composed of 4 distributions (lumen, intima, media, and surrounding tissues), but a skilled reader will easily understand that the EM algorithm is general and may estimate more PDF distributions of heterogeneous vessel layers if required.

Testings were conducted on in-vivo blood vessels and numerical simulations of blood vessel IVUS data. The in-vivo B-mode IVUS images were segmented with 3D multiple interface fast marching using automatically detected gray level Rayleigh PDFs and, as a comparison, using the gray level gradient. All catheter pullbacks were segmented three times with both 3D methods using different sets of initial contours. Lumen, intima (plaque), and media boundaries were obtained. To quantify the variability of boundary detection under various initializations, average and Haussdorf point-to-point distances, as disclosed by Chalana et al., in "A methodology for evaluation of boundary detection algorithms on medical images" (*IEEE Trans. Med. Imag.*, vol. 16, no. 5, pp. 642-652, 1997), between resulting contours from different initial contour sets were calculated. Haussdorf distance represents the worst case since it generates the maximum distance between different segmentation results. Average and Haussdorf distances directly depict point-to-point contour variations.

Detected boundaries from a whole IVUS catheter pullback represent a blood vessel in 3D that can be reconstructed. Reconstruction of the lumen and media contours was made from a simple, smoothed contour stack (see FIG. 11).

In addition to the above-described in-vivo validation of the illustrative embodiment of the segmentation method, numerical simulations of IVUS data were conducted to evaluate segmentation accuracy. Since the exact geometry of the simulated data is generally entirely known, direct performance calculations of the detected boundary with respect to the exact geometry of the simulated data can be obtained. The simulated B-mode IVUS data were first segmented using the same procedure as for the in-vivo data, also including 3 different sets of initial longitudinal view generating initialization contours. Lumen, intima (plaque), and media boundaries were obtained. Average and Haussdorf point-to-point distances between detected contours and ground truth boundary position were calculated for the segmentation results from each set of initial contours.

Because the simulation method described in FIG. 6 allows synthesizing both RF and B-mode IVUS data, the hereinabove described fast-matching segmentation method was also tested by using automatically detected gray level Gaussian PDFs from the 3D simulated RF images.

The image-formation model that was used to simulate IVUS data (echograms) is detailed by Maurice et al., in "Adapting the Lagrangian speckle model estimator for endovascular elastography: Theory and validation with simulated radio-frequency data" (*J. Acoust. Soc. Am.*, vol. 116, pp. 1276-1286, 2004). Under assumptions such as space-invariance of the imaging system, IVUS images were modeled by a convolution operation between the point-spread function, which is the equivalent radio-frequency image of a single ultrasound scatterer, and the function describing the acoustic impedance mismatch of each scatterer of the simulated tissue structures composing the IVUS data. In other words, the point-spread function expresses the intrinsic characteristics of the ultrasound imaging system.

The implementation of the image-formation model was made for a 20 MHz transducer with a 60% bandwidth at −3 dB and a beam width of 0.1 mm. For the purpose of these simulations, the media was selected 2 times more echogenic than the lumen; the plaque, 1.5 times more echogenic than the media; and the surrounding tissues 2 times more echogenic than the media. The echogenicity can be seen as the image intensity reflecting the acoustic impedance mismatch of the scatterers. The signal to noise ratio (SNR) was set to 20 dB.

Figure 6:
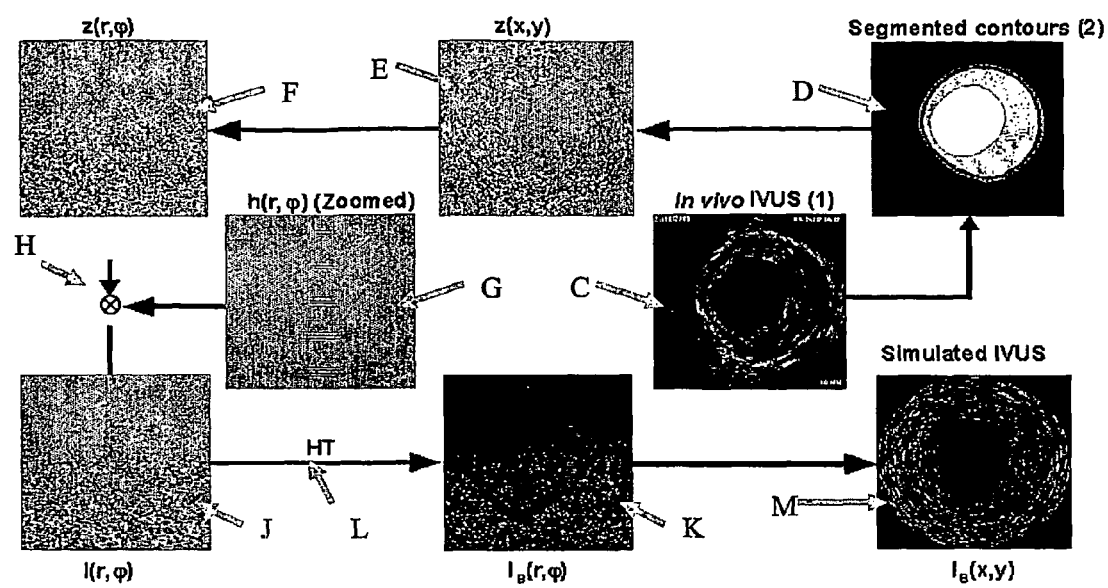
FIG. 6 is a flowchart schematically representing simulated IVUS image data generated from a plurality of 2D IVUS frames as the one shown in FIG. 1.

FIG. 6 shows the image formation model used to simulate RF and B-mode IVUS data. From real 2D in vivo IVUS images, as the one shown in box C, the segmented contours or vessel boundaries (lumen, plaque of the intima, media) are created (box D) from manually traced contours on the IVUS 2D image in box C. Box E shows the function $z(x,y)$ representing the acoustic impedance variations within the 2D frame from box D, and box F shows a function $z(r,\phi)$ expressing the same acoustic impedance variations mapped within the 2D frame in polar coordinates. Box G shows the polar point spread function $h(r, \phi)$ with a beam width that increases with depth and element H is a 2D-convolution operator. Processing of function $z(r,\phi)$ (box F) with the polar point spread function $h(r, \phi)$ (box G) through the 2D-convolution operator (element H) produces a simulated polar radio-frequency (RF) image $I(r,\phi)$ (box J). Box K illustrates the polar B-mode image $I_B(r, \phi)$ that was computed using the Hilbert transform (see element L) of $I(r,\phi)$, as presented by Kallel et al. in "Speckle motion artifact under tissue rotation." (*IEEE Trans. Ultrason., Ferroelect., Freq. Contr.*, vol. 41, pp. 105-122, 1994). Box M shows the Cartesian B-mode image or simulated IVUS image $I_B(x, y)$ calculated from the polar B-mode image $I_B(r, \phi)$. This simulation strategy was repeated for the whole image data of an IVUS catheter pullback within a diseased superficial femoral artery.

Results and Discussions

As stated hereinabove, the EM algorithm was applied 10 times on 1 IVUS catheter pullback to evaluate the robustness of the PDF mixture parameter estimation. At each run, PDF parameters were estimated on different pixel subsets of the same IVUS data (subsets contained approximately 400 000 pixels). Average mixture parameters for each detected Rayleigh PDF are shown in the following Table I. An example of automatically detected Rayleigh PDF mixture is also shown in FIG. 3 in dotted lines for each layer components, with the hereinbefore presented IVUS pullback gray level histogram of the whole data set.

TABLE I

| Layer Component | ω (%) | $a^2$ |
|---|---|---|
| Lumen | 29.40 ± 0.10 | 0.6456 ± 0.0021 |
| Intima and Plaque | 20.96 ± 0.50 | 347.70 ± 13.02 |
| Media | 13.55 ± 0.14 | 22.68 ± 0.53 |
| Surrounding Tissues | 36.09 ± 0.67 | 2294.58 ± 34.01 |

Table I shows that small variations were found between different runs of the EM algorithm. It can be stated that mixture detection of the various boundary layers is a robust and stable process with standard deviations of ω and $a^2$ ranging from 0.3% to 3.7% for several runs of the EM algorithm applied on different pixel subsets of the IVUS catheter pullback. The EM algorithm was thus applied to the 8 available IVUS catheter pullbacks to study PDF variability between different patients. The results are shown in the following Table II.

TABLE II

| Layer Component | ω (%) | $a^2$ |
|---|---|---|
| Lumen | 18.82 ± 10.44 | 5.52 ± 12.50 |
| Intima and Plaque | 27.81 ± 14.54 | 1052.40 ± 1405.97 |
| Media | 15.87 ± 3.61 | 339.46 ± 817.80 |
| Surrounding Tissues | 37.50 ± 13.82 | 2580.49 ± 654.49 |

Because of instrument settings and echogenicities specific to the different vascular structures for a given patient, Table II emphasizes the generally high variability between mixture parameters of distinct IVUS catheter pullbacks. These results suggest that the EM algorithm is capable of fitting various Rayleigh PDF mixtures from different patients.

The numerically simulated and in-vivo IVUS images can then be segmented with 3D multiple interface fast marching methods using automatically detected gray level PDFs and gray level gradient for comparison purposes. For the experimental testing, all IVUS catheter pullbacks were segmented three times with both 3D methods using different sets of initial interfaces obtained from the initialization contours generated from the longitudinal planes.

The results obtained for the simulated segmentation of the IVUS images with the detected gray level Rayleigh PDFs method and with the gray level gradient method are shown in FIGS. 7a to 8d. FIGS. 7a to 7d are concerned with a first blood vessel geometry, shown in FIG. 7a, and FIGS. 8a to 8d are concerned with a second blood vessel geometry shown in FIG. 8a.

FIGS. 7b and 8b respectively show the simulated IVUS cross-sectional 2D B-mode images of the first and second examples of a simulated blood vessel, which can be obtained from the above-described method schematically illustrated in FIG. 6. In FIGS. 7c and 8c, the detected boundaries of the lumen, the thickened intima and media are estimated with the detected gray level PDFs method and, in FIGS. 7d and 8d, with the gray level gradient method.

The typical simulated IVUS segmentation results shown in FIGS. 7a to 8d illustrate that detected boundaries were very close to the blood vessel layer boundaries. They also reveal that the external boundary of the media is smoother with the PDF fast marching than the gradient-based method, but that the lumen, which can have a rougher surface, was detected with sufficient details. Gradient methods seemed to trace speckle contours on object boundaries, because speckle generally has high gray level intensity differences.

The following Table III includes the results of the average distance (AD) and Haussdorf distance (HD), which is the maximum distance between the estimated boundary and the true boundary in mm, between detected boundaries obtained from different initialization steps and ground truth values (true boundaries) obtained from the simulated geometry. In this table, FMM refers to the fast marching segmentation method. Symbol * indicates a statistically significant better performance with $p<0.05$ on paired t-test, whereas symbol § refers to a statistical significance of $p<0.01$.

TABLE III

| Segmentation Method | Lumen | | Plaque | | Media | |
|---|---|---|---|---|---|---|
| | AD (mm) | HD (mm) | AD (mm) | HD (mm) | AD (mm) | HD (mm) |
| FMM-3D PDFs | 0.072 ± 0.062 | 0.226 ± 0.074 | 0.061 ± 0.038 | 0.154 ± 0.046* | 0.063 ± 0.038 | 0.164 ± 0.048§ |
| FMM-3D Gradient | 0.069 ± 0.056§ | 0.197 ± 0.085§ | 0.060 ± 0.044 | 0.173 ± 0.050 | 0.063 ± 0.044 | 0.180 ± 0.052 |

The average and Haussdorf distance were chosen as comparison metrics instead of area or perimeter differences because they directly depict point-to-point contour variations. As can be seen in Table III, very low average and Haussdorf distances values were obtained, for both PDF- and gradient-based three-dimensional (3D) fast marching, demonstrating that the method is very powerful for simulated B-mode IVUS segmentation. In fact, average deviation ranged from 0.060 to 0.072 mm and worst point-to-point distances were between 0.154 and 0.226 mm, which is highly satisfactory. Lower Haussdorf distances were obtained on lumen boundary with the gradient method ($p<0.01$) because the blood and intima interface generally produces bright echoes for which the gradient information is significant. However, on less contrasting boundaries such as the intima (plaque) and media interfaces, statistically significant lower Haussdorf distances ($p<0.05$) were achieved with the PDF-based method.

Examples of results obtained with the gray level Rayleigh PDF method and with the gray level gradient method for the in-vivo IVUS data are displayed in FIGS. 9a to 10c. The lumen, intima and media detected boundaries are presented for a first cross-sectional IVUS image (FIG. 9a) and a second different cross-sectional IVUS image (FIG. 10a).

In FIGS. 9b and 10b, the detected boundaries of the lumen, the intima and media are estimated with the gray level PDF based fast-marching method and, in FIGS. 9c and 10c, with the gray level gradient based fast-marching method.

A qualitative analysis of the gray level PDF and gray level gradient fast marching segmentation methods reveals that the detected boundaries are very close to all vessel layers. More specifically, FIGS. 9a to 10c show that vessel layer boundaries of in-vivo IVUS images can be identified even if the contrast is very low, as illustrated at 4 o'clock for the collateral vessel in FIG. 9a. Also, detected boundaries on FIGS. 10b and 10c demonstrate that non-circular lumen may be detected with fast marching methods.

The following Table IV shows the average distance (AD) and the Haussdorf distance (HD) between detected boundaries on in-vivo data for the gray level PDF and gray level gradient fast marching methods for different manual initializations of the interfaces.

TABLE IV

| Segmentation Method | Lumen | | Plaque | | Media | |
| --- | --- | --- | --- | --- | --- | --- |
|  | AD (mm) | HD (mm) | AD (mm) | HD (mm) | AD (mm) | HD (mm) |
| FMM-3D PDFs | 0.092 ± 0.095 | 0.270 ± 0.147* | 0.092 ± 0.078 | 0.256 ± 0.102§ | 0.092 ± 0.083 | 0.256 ± 0.113* |
| FMM-3D Gradient | 0.092 ± 0.104 | 0.317 ± 0.148 | 0.090 ± 0.080* | 0.287 ± 0.092 | 0.085 ± 0.088* | 0.302 ± 0.107 |

In Table IV, FMM refers to the fast-marching segmentation method, symbol * indicates a statistically significant better performance with $p<0.05$ on paired t-test, whereas symbol § means a statistical significance of $p<0.01$.

Results indicate that gray level PDF fast marching has the smallest Haussdorf distances ($p<0.01$), which remains under 0.270 mm for all boundaries compared to a value of up to 0.317 mm for the gray level gradient implementation. PDF fast marching also has relatively small average distances between contours, of 0.092 mm and lower, but are significantly higher than intima and media average distances obtained with the gray level gradient method ($p<0.05$). However, the differences between these distances are generally small (lower than the pixel size). Thus, 3D fast marching detected boundaries have small variations when initialized differently and the maximum distance to the closest point, representing the worst case, generally stays low. This tends to indicate that the segmentation performance is good in regions lacking information, for example when the boundaries to be detected are covered with catheter ring-down artifacts of lost behind calcium deposits.

FIG. 11 shows a 3D reconstruction of the lumen and media contours obtained with gray level PDF 3D fast marching segmentation for which a double stenosis in that patient is clearly seen. In the figure, the light gray corresponds to the inner portion of the media, whereas the dark gray is the vessel lumen. The gray level gradient fast marching method provided similar qualitative results (data not shown).

As mentioned hereinabove, the PDF-based fast-marching segmentation method can further exploit RF data in place of B-mode data. On RF data, the EM algorithm generally searches for a mixture of Gaussian PDFs describing the different layered structures of the vessel wall on IVUS images.

FIG. 12a shows a simulated 2D RF image taken from the whole 3D data set, whereas FIG. 12b presents an example of segmentation results obtained with the PDF method applied on RF IVUS data. Qualitatively, similar performance can be appreciated when comparing those results to FIG. 8c. However, quantitatively, better accuracy is generally expected because of the higher resolution of RF images when compared to B-mode data.

In a preliminary version of the IVUS fast marching segmentation method disclosed by Roy Cardinal et al., in "Intravascular ultrasound image segmentation: A fast marching method" (*Lecture Notes in Computer Sciences. Proceedings of MICCAI* 2003: *Medical Image Computing & Computer Assisted Intervention*, vol. 2879, 2003, pp. 432-439), a 2D version of the fast marching method was implemented.

Generally speaking, a 2D IVUS algorithm uses segmentation from previous IVUS images of the catheter pullback to correct initial interfaces. The 2D segmentation model disclosed by Roy Cardinal in the above-mentioned study was applied to a small IVUS catheter pullback of 200 images. Depending on the IVUS application, any dimensions can be considered for implementing the fast-marching PDF or gradient based method. The present multi-dimensional method is general and conceptually considers 1D to ND dimensions, where N is the order of the method. Note that N=4 considers time varying 3D IVUS data.

Since a bigger IVUS B-mode clinical database was available for the present study, the 2D version of the fast marching segmentation was applied to all available catheter pullbacks. The 2D implementation of fast marching arrival time (from Equation 10) and speed functions (from Equations 11 and 12) is generally straightforward. In 2D, 8-connected pixels (26 connected pixels for the hereinabove presented method) were used for averaging neighbors in the speed function calculation.

The following Table V shows the average distance (AD) and the Haussdorf distance (HD) between boundaries of the detected vessel layers, from different initializations with 2D fast-marching segmentation. As for the 3D fast marching method, the results are for automatically detected PDF- and gradient-based algorithms.

TABLE V

| Segmentation Method | Lumen | | Plaque | | Media | |
|---|---|---|---|---|---|---|
| | AD (mm) | HD (mm) | AD (mm) | HD (mm) | AD (mm) | HD (mm) |
| FMM-2D PDFs | 0.093 ± 0.096 | 0.279 ± 0.149 | 0.093 ± 0.078 | 0.262 ± 0.102 | 0.091 ± 0.083 | 0.262 ± 0.113 |
| FMM-2D Gradient | 0.096 ± 0.106 | 0.316 ± 0.147 | 0.095 ± 0.088 | 0.299 ± 0.100 | 0.085 ± 0.090 | 0.304 ± 0.104 |

A two way analysis of variance with pairwise multiple comparisons using the Turkey test was performed on average and Haussdorf distances for 2D (Table V) and 3D (Table IV) fast marching.

Statistical tests showed that average distances from the 2D fast marching detected boundaries in Table V were not different from the 3D fast marching results for all blood vessel layers. It should be noted that 2D algorithms used segmentation from previous images of the catheter pullback to correct initial contours, which increased boundary precision. Thus, alternatively, the segmentation performance can be increased by combining this type of correction strategy in the 3D fast marching method, by using a multi-scale segmentation approach to initialize a higher resolution data set with low resolution segmentation results of the same catheter pullback. As for the 3D fast marching method, the gray level PDF fast marching in 2D had lower Haussdorf distances than the gray level gradient method ($p<0.05$). Since good average distance performance was achieved with the gray level gradient method in both 2D and 3D fast marching, this information can be added with advantage to the PDF speed function of Equation 11.

A second non-restrictive illustrative embodiment of the method and device according to the present invention will now be described. For the sake of brevity, only the differences between the method and device according to the first non-restrictive illustrative embodiment and the second non-restrictive illustrative embodiment are described hereinbelow.

In the second non-restrictive illustrative embodiment, the fast marching method has been modified to enhance the efficiency in computing time. In the fast marching method in accordance with the first illustrative embodiment, several interfaces simultaneously propagate across the IVUS image data. In the propagation process, the propagating interfaces and their neighboring areas are explored in a significantly detailed manner. Generally, in the segmentation method as described in the first illustrative embodiment, all pixels are analyzed and the propagation process takes into account all preceding interface neighbors through the arrival time map construction. Computation time is thus increased as the initial interface propagates in a larger initial segmentation area.

In the first illustrative embodiment, the position of the initial interfaces is calculated from a shrunk version of manually or automatic traced initialization contours taken along a longitudinal plane. Examples of the position of initial interfaces calculated from initialization contours are shown in FIGS. 13a and 13b.

The black region represents the unexplored propagating area 130, the gray pixels on each side of the propagating area 130 correspond to the propagating interfaces 132,134 and the arrows 136a,136b,136c and 136d represent the propagation direction of the propagating interfaces 132,134. The dashed line 138 represents the desired boundary to reach and the solid line is an example of initial interface 140 from which the initial propagating interfaces 132, 134 were calculated. In FIG. 13a, the interfaces will not detect the boundary 138 because the propagation area 130 was not set wide enough to completely include the boundary 138, as in FIG. 13b. However, propagation in FIG. 13a will be completed faster than the case of FIG. 13b.

Therefore, to decrease computational load, shrinking can be diminished to create a smaller propagating area 130 (FIG. 13a). However, because the fast marching method propagates an interface 132,134 under a unidirectional speed function (see arrows 136a,136b or 136c,136d) the boundary 138 to be detected must be located inside the propagating area 130 that will be explored during the propagation.

A compromise between the dimension of the propagating area 130 and the computation time is sought. With known 2D fast marching segmentation method, this problem is generally solved by using segmentation results from previous 2D images of the catheter pullback to correct initial interfaces. The initial interfaces 140 are then more precise and the propagating area 130 can be set with smaller dimensions.

In the 3D fast marching segmentation method of the first non-restrictive illustrative embodiment, a correction similar to this 2D correction principle can be made through a multi-resolution or multi-scale representation and segmentation of the IVUS data. An example of such multi-resolution images in IVUS data is shown in FIGS. 14a-14d, where lower resolution images are obtained by undersampling the original IVUS image by $2^l$ (Operation 191 of FIG. 20) where l=3, 2, 1, 0 is the resolution level corresponding to FIGS. 14a, 14b, 14c and 14d, respectively. High scale structures, such as for example the lumen, are generally emphasized on lower resolution images.

Figure 20:
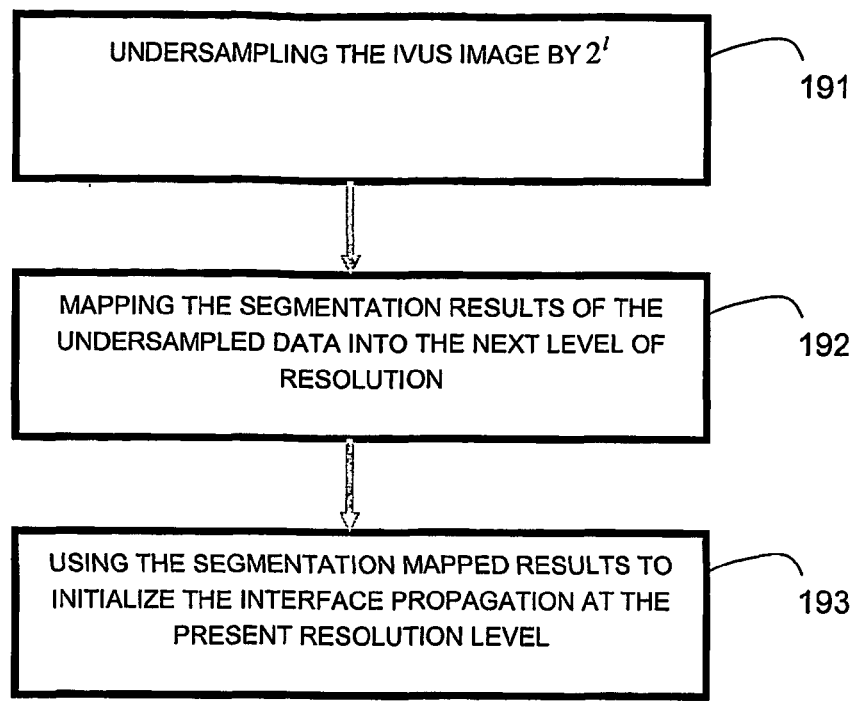
FIG. 20 is a flowchart representing an IVUS method for initializing propagating interfaces generated from lower resolution segmentation results according to the second illustrative embodiment of the present invention.

The segmentation results of a lower resolution representation of the IVUS data are mapped into the next level of resolution (Operation 192 of FIG. 20). Boukerroui et al., in "Segmentation of ultrasound images—multiresolution 2D and 3D algorithm based on global and local statistics" (Pattern *Recognition Letters*, 24:779-790, 2003) and Mignotte et al., in "A multiscale optimization approach for the dynamic contour-based boundary detection issue" (Computerized Medical Imaging and Graphics, 25(3):265-275, 2001) propose related concepts.

These segmentation-mapped results are used to initialize the interface propagation at this higher resolution level (Operation 193 of FIG. 20). At a low-resolution level, a fast coarse exploration of a wide propagating area is performed to bring the propagating interfaces 132,134 closer to the desired boundaries 138 (Operation 201 of FIG. 21). The propagation area 130 can then be reduced at each higher resolution level since the interfaces 132,134 are iteratively corrected (Operation 202 of FIG. 21). A larger propagation area 130 can thus be explored in less calculation over all possible resolutions.

At a resolution level l, a pixel represents a $2^l \times 2^l$ block of pixels from the original resolution image. In FIGS. 14a to 14d, the undersampling that was used resulted in loss of information at low resolution levels. To overcome this loss of information, a multiscale PDF-based velocity function (similar to Equation 11) is developed and used (Operation 203 of FIG. 21), where $P(T_s)$ is replaced with the likelihood of the $2^l \times 2^l$ block of pixels corresponding to $I_s$ when the propagation is done at level l, as given by equation 13:

$$P(I_s) = \prod_{s_l \in b_l} P(I_{s_l}) \tag{13}$$

where $b_l$ is the block of $2^l \times 2^l$ pixels and $P(I_{s_l})$ is the occurring probability of the gray level value of pixel $s_l$ in the zero resolution image l.

Figure 21:
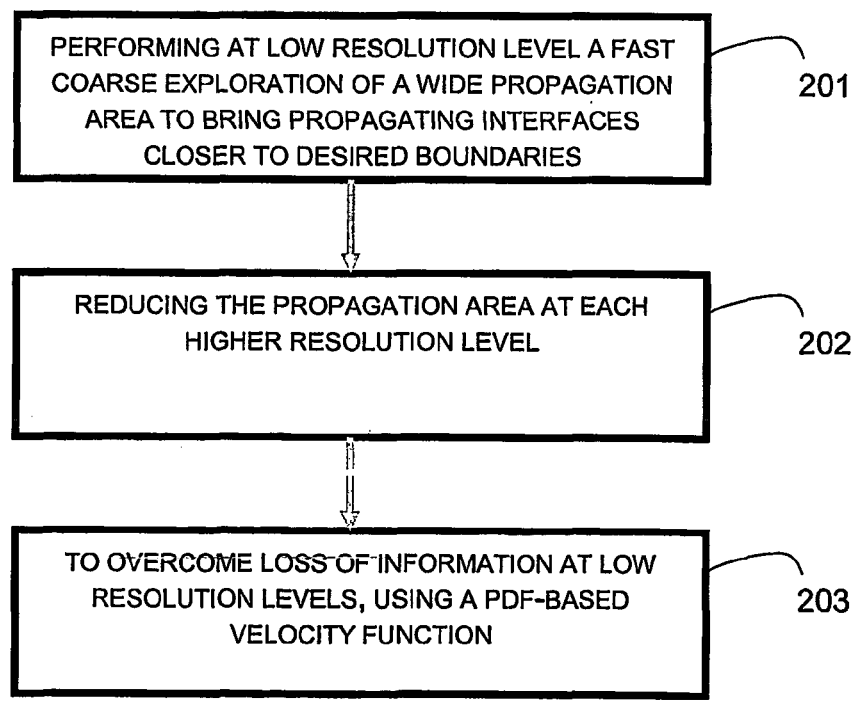
FIG. 21 is a flowchart representing an exploration method from a wide propagating area at low resolution to a reduced propagating area at high resolution according to the second illustrative embodiment of the present invention.

The multiresolution and multiscale fast marching segmentation methods of FIGS. 20 and 21 generally allows to iteratively improve the accuracy of the detected boundaries without increasing the computation time.

A third non-restrictive illustrative embodiment of the method and device according to the present invention will now be described. For the sake of brevity, only the differences between the third non-restrictive illustrative embodiment and the first non-restrictive illustrative embodiment will be described hereinbelow.

In this third non-restrictive illustrative embodiment, the fast marching method has been modified to automatically find the initial interfaces for the layers of the vessel wall (lumen, inside and outside contours of the media) by using likelihood maps of each components of the vessel wall (lumen, intima and plaque, media, and surrounding tissues), which are calculated according to the estimated PDF mixture parameters. This approach can be seen as an alternative to the manual initializations of the vessel interfaces described hereinabove.

The initialization procedure generally finds a rough estimate of the true boundaries of the layers that will be further refined into accurate wall contours with the multiresolution or multiscale gray level PDF fast marching method.

Figure 22:
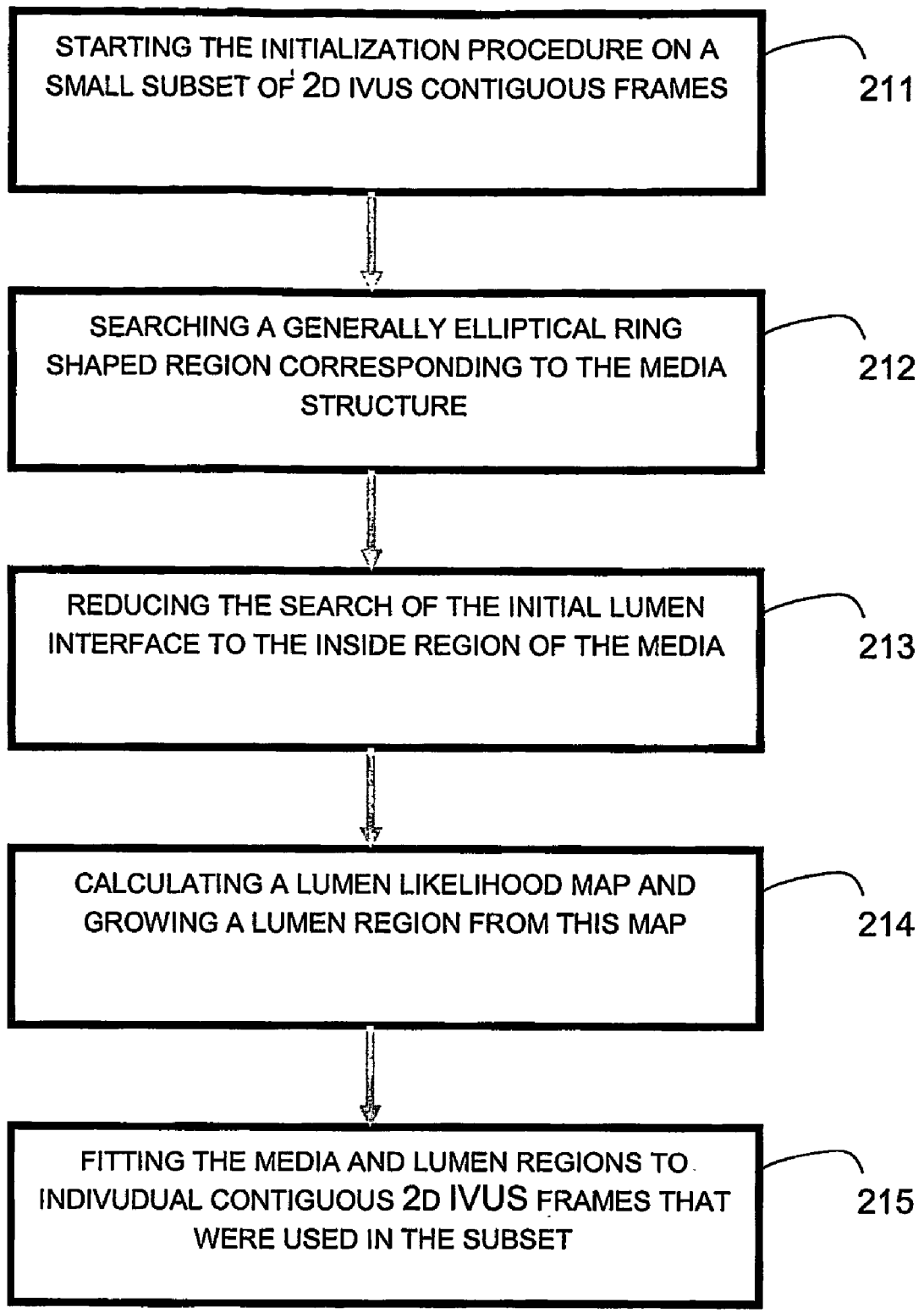
FIG. 22 is a flowchart representing a template region searching method for automatically finding initial interfaces of the layers according to the third illustrative embodiment of the present invention.

The initialization procedure generally starts on a small subset of contiguous 2D IVUS frames from the whole catheter pullback (Operation 211 of FIG. 22). For instance, the subset may contain $N_{init}$ 2D IVUS frames to get as much information as possible ($N_{init}$=ten (10) for example), while keeping enough correlation between the 2D IVUS frames. For better results, the selected 2D IVUS frames are generally of good quality, with no calcification shadows and with a generally homogeneous plaque, in order to maximize the available information for determining the initial interface.

To find these good quality 2D IVUS frames, a degree of fitting is first calculated between each of the individual frame histogram and the pullback PDF mixture (see FIG. 3). The degree of fitting can be measured by the Kolmogorov-Smirnov test that calculates the distance between the PDF mixture and the normalized histogram of an IVUS 2D frame. This test is used to determine if an empirical distribution (IVUS histogram) differs from a theoretical distribution (mixture). The Kolmogorov-Smirnov distance, between the subset init of $N_{init}$ images and the global IVUS data PDF P, that should be minimized is:

$$K = \sum_{j \in init} \sum_{s \in I} \left| \frac{k_j(I_s)}{N} - P(I_s) \right| \tag{14}$$

where $I_s$ is the gray level value of pixel s in image I; $k_j(I_s)$ is the number of pixels having the gray level value $I_s$ in the $j^{th}$ image of the subset; and N is the number of pixels in image I.

The contiguous frames having the smallest Kolmogorov-Smirnov distances are generally chosen. Since the mixture is calculated over the whole catheter pullback, it represents the average lumen and blood vessel wall. This test thus generally selects the frames that are similar to the average catheter pullback, and these frames are used to start the calculation of the initial interface.

Calculation of the initial interface is initiated with the search of an inner generally elliptical ring shaped region corresponding to the media structure 150 (Operation 212 of FIG. 22), as shown in FIG. 15. This media region 150 is distributed according to the hereinabove disclosed media PDF and enclosed between a surrounding tissue region 152 and a plaque region 154. The media region 150, the surrounding tissue region 152 and the plaque region 154 are generally of fixed size to simplify the initialization procedure and because only a rough estimate of the media is generally necessary. The surrounding tissue region 152 and the plaque region 154 do not have to represent the whole plaque and surrounding tissues since they are defined to provide additional information about the media region 150.

The initialization procedure generally begins with the search of the media region 150 of the blood vessel because it is believed that the elliptical constraints are more easily assumed for this layer. It was indeed reported by Hagenaars et al., in "Gamma radiation induces positive vascular remodeling after balloon angioplasty: A prospective, randomized intravascular ultrasound scan study" (Journal of Vascular Surgery, 36(2):318-324, 2002) in which 15 patients out of 16 had a dissection after angioplasty of the femoropopliteal artery making the lumen irregularly shaped.

Since IVUS data acquisition is often conducted in atherosclerosis treatment trial in which patients undergo angioplasty, the irregularities of the layers should be taken into account. Also, the search of the initial lumen interface is reduced to the inside region of the media (Operation 213 of FIG. 22), which generally prevent the propagating interface from leaking into collateral branches when they are present. Moreover, the elliptical shape of the initial media region 150 generally produces a closed initial interface, even if the media is hidden behind a calcification shadow.

In order to find the media region 150 in the subset of initial IVUS frames, an energy function must be associated with the template 158 of FIG. 15. In the deformable model framework disclosed by Jain et al., in "Deformable template models: A review" (Signal Processing, 71(2):109-129, 1998) and by Zhong et al., in "Object tracking using deformable templates" (In Sixth International Conference on Computer Vision; pages 410-445, 1998), the energy function is generally defined to be minimal when the template fits the searched region. Deformations are applied to the template 158 to achieve a minimum energy function on the image.

The energy function that should be minimized to find the media region 150 is given by the following Equation 15:

$$\varepsilon(R, I_s) = -\sum_{r_l \in R} \left( \frac{1}{N_{r_l}} \sum_{j=1}^{N_{init}} \sum_{s \in r_l} \log P(I_s^j | r_i) \right) \tag{15}$$

where $P(I_s^j | r_i)$ is the occurring probability of the gray level value of pixel s in the $j^{th}$ IVUS image of the initial subset according to the PDF of region $r_i$; $R = \{r_p, r_m, r_t\}$ are the plaque region ($r_p$) 154, media region ($r_m$) 150 and tissue region ($r_t$) 152 of the template 158; $N_{init}$ is the size of the initial frame subset.

Generally only linear transformations such as for example translations, stretchings, and rotations are applied to the template 158 because only a generally rough estimate of the media region 150 is needed. The template 158 fitting is performed at a reduced resolution level l=1, as described in the second non-restrictive illustrative embodiment, in order to minimize the computation time, while keeping a large enough media to work with. Different known minimization algorithm can be used for minimizing the deformation model.

The lumen region (not shown in FIG. 15) is then searched from the defined initial media boundary. A region without geometrical shape constraints is computed: the lumen likelihood map is calculated and a lumen region is grown or propagated using this map (Operation 214 of FIG. 22). The lumen region generally starts at the IVUS catheter that is inside the lumen and generally located in the vicinity of the center of all pullback frames.

The lumen region grows by adding the pixels that are most likely to be inside the lumen according to the occurring probability, for example if the log-likelihood $$-\sum_{j=1}^{N_{init}} \log P(l_s^j \mid r_l)$$

of pixel s in the $N_{init}$ image subset according to the PDF of the lumen region $r_l$ is low enough. The region is generally forbidden to grow beyond the boundary of the media region 150.

The media and lumen regions are then adjusted or fitted to the $N_{init}$ contiguous 2D IVUS frames that were used in the initial subset (Operation 215 of FIG. 22). Linear transformations may be applied to these media and lumen regions to maximize their likelihood to each of the contiguous 2D IVUS frames. This step is usually performed as for the hereinabove described media deformable template, but the initial intima and plaque region 154 is bounded by the lumen region and the media region 150, and the initial surrounding tissues region 152 is bounded on only one side by the media region 150.

This procedure is generally repeated for the next subset of contiguous 2D IVUS frames in the catheter pullback. However, the process for each contiguous 2D IVUS frame generally starts with the results of the previous defined media template 158. The growth of the lumen region generally starts from a shrunk version of the previous average lumen region. The whole IVUS image pullback is therefore initialized in that manner.

Alternatively, the segmentation fast marching method as described in the first illustrative embodiment may use a combination of the gray level gradient information and the gray level PDF information in the calculation of the initial interfaces if using only the gray level PDF information turns out to be insufficient to generate an automatic initialization as described in the third illustrative embodiment. The gray level gradient information could also be integrated to the interface velocity function of Equation 11.

In the case of very low-quality images or high ultrasound attenuation limiting penetration within the vascular wall, the proposed initial boundary calculation procedure might fail to find some initial contours or region boundaries. For these particular cases, minimal user interaction might be required to correct some regions of the interfaces. If necessary, this interaction may further be included in the segmentation process to minimize the occurrences of having to re-segment accurately found boundaries.

In the case where a single boundary is available, such as for example the boundary between the lumen and the intima, the elliptical template may be modified in such a way as to provide a two (2) region template generally corresponding to the regions between the single boundary. The energy function of equation 15 thus becomes generally restrained to two (2) regions and the remaining initialization procedure remains generally similar to the case of the multiple boundary initialization.

A fourth non-restrictive illustrative embodiment of the method and device according to the present invention will now be described. For the sake of brevity, only the differences between this fourth illustrative embodiment and the first illustrative embodiments will be described.

In this fourth non-restrictive illustrative embodiment, the fast marching method has been modified to replace the EM local algorithm presented in the first illustrative embodiment. The EM algorithm is a local algorithm in which the neighbors information is missing. This information is generally required, such as for example, in the case of heterogeneous plaque where the PDFs are generally more difficult to estimate. In addition, convergence is generally very slow with the EM algorithm such that it can take a significant number of iterations in order to be able to estimate the mixture parameter $\Theta$ of Equation (2).

The automatic initial contour detection procedure presented in the previously presented third illustrative is based on the IVUS PDF information. In cases where the EM algorithm cannot be used, the iterative conditional estimation (ICE) algorithm that was previously proposed for the mixture parameter estimation of incomplete data by Pieczynski in "Champs de markov cachés et estimation conditionnelle iterative" (Traitement du Signal, 11(2):141-153, 1994) generally represents a more robust algorithm, which generally converges faster than the EM algorithm.

In the PDF mixture estimation presented in the first illustrative embodiment, the random variables (X, Y) are referred to as the complete data where Y is the gray level taking values in [1, ..., 256] (observed data), and X is the tissue label taking values [1, ..., M] for a PDF mixture modeling M different tissues (hidden information). For the set of pixels S, the realization $y=(y_s)_{s \in S}$ of Y is the IVUS B-mode or RF image and $x=(x_s)_{s \in S}$ are the unknown pixel labels. The EM algorithm is considered local because the labels $x_s$ are considered independent. In the ICE algorithm, X is supposed Markovian i.e. $P_X(x)$ is defined with respect to the following neighborhood energy function:

$$P(x) = \exp\left(-\sum_{\langle s,t \rangle} \phi(x_s, x_t)\right) \quad (16)$$

where $\phi$ is an energy function and the summation is for all pairs of pixel neighbors $\langle s,t \rangle$.

Figure 23:
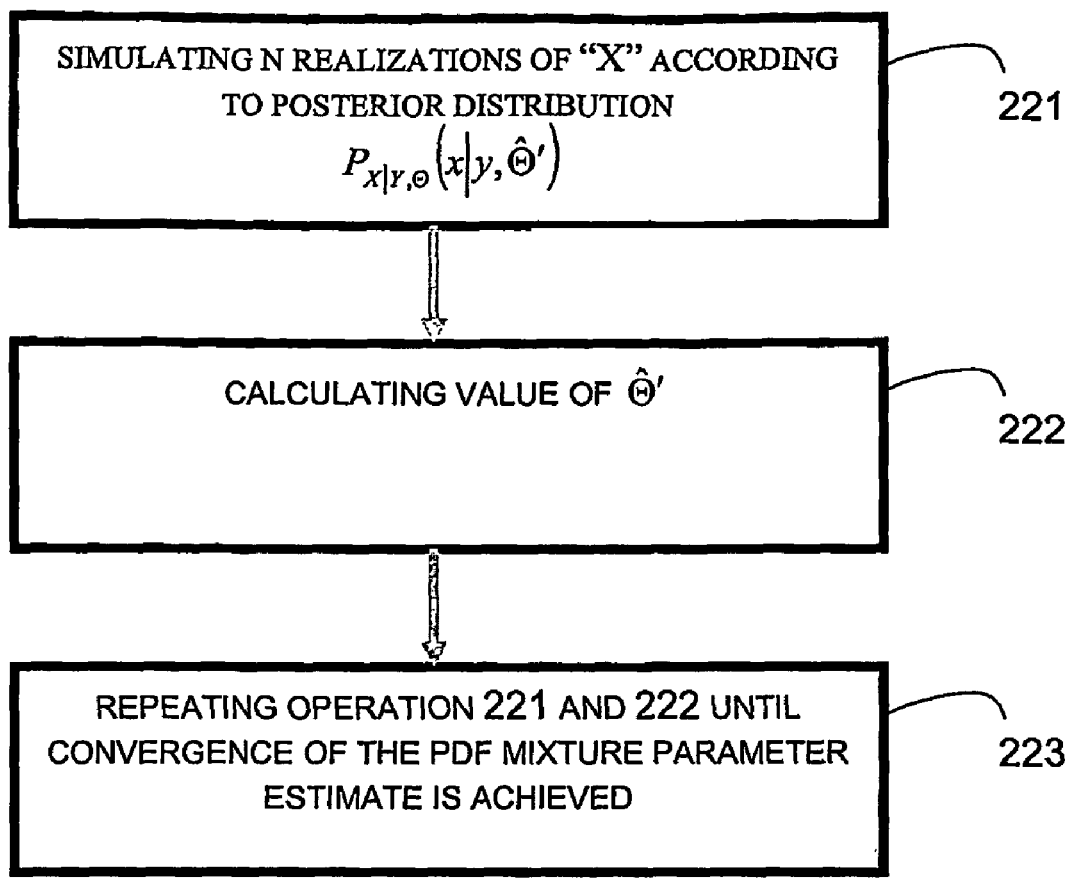
FIG. 23 is a flowchart representing an automatic estimation method of the probability density function mixture parameters based on the iterative conditional estimation according to the fourth illustrative embodiment of the present invention.

The first operation of the ICE algorithm is to simulate, such as for example with the Gibbs sampler, n realizations $(x_1, \ldots, x_n)$ of X according to the posterior distribution $P_{X|Y,\Theta}(x|y,\hat{\Theta}')$, with $\hat{\Theta}'$ the initial or the previous iteration estimate of the PDF mixture parameter $\Theta$ (Operation 221 of FIG. 23). The posterior distribution is computed using Bayes rule from the known $P_X(x)$ and $P_{Y|X,\Theta}(y|x, \hat{\Theta}')$; and the neighborhood $V_s$ of pixel s:

$$p_{\hat{\Theta}'}(x_s | y_s) = \frac{\exp\left(-\sum_{t \in V_s} \phi(x_s, x_t) - \log p_{\hat{\Theta}'}(y_s | x_s)\right)}{\sum_{k=1}^{M} \exp\left(-\sum_{t \in V_s} \phi(x_s = k, x_t) - \log p_{\hat{\Theta}'}(y_s | x_s = k)\right)} \quad (17)$$

With these simulations of the hidden data, n sets $((x_1, y), \ldots, (x_n, y))$ of complete data are available.

The next operation (Operation 222 of FIG. 23) is to calculate the new value of $$\hat{\Theta}' = \frac{1}{n}[\hat{\Theta}(x_1, y) + \ldots + \hat{\Theta}(x_n, y)],$$

where $\hat{\Theta}$ is a parameter estimator of the complete data (maximum likelihood for example). Operations 221 and 222 of FIG. 23 are generally repeated until convergence of the mixture parameter estimate is achieved (Operation 223 of FIG. 23).

For the Rayleigh mixture, it is assumed that each layer structure of the B-mode images is a generally uniform scattering tissue with a significantly large number of diffusers because the Rayleigh PDFs model the gray level distribution of the ultrasound signal under that condition, as disclosed by Wagner et al., in "Statistics of speckle in ultrasound B-scans" (IEEE Transactions on Sonics and Ultrasonics, 30(3):156-163. 1983). The same reasoning applies to Gaussian PDFs describing RF IVUS images.

In the case of highly heterogeneous plaque layer of a diseased patient, the Rayleigh or Gaussian PDF might not be sufficient to model the pixel gray level distribution. Distributions other than Rayleigh or Gaussian have been investigated in modeling of the ultrasound B-mode envelopes or RF signals, respectively: Rician distribution as disclosed by Wear et al., in "Statistical properties of estimates of signal-to-noise ratio and number of scatterers per resolution cell" (Journal of the Acoustical Society of America, 102(1):635641, 1997), K distribution as disclosed by Dutt et al., in "Statistics of the log-compressed echo envelope" (Journal of the Acoustical Society of America, 99(6):3817-3825; 1996) and Nakagami distribution as disclosed by Shankar in "A general statistical model for ultrasonic backscattering from tissues" (IEEE Transactions on Ultrasonics, Ferroelectrics, and Frequency Control, 47(3):727-736, 2000).

The ICE algorithm generally has no limitation for the type of statistical distribution to be modeled, as long as a parameter estimate of the complete data can be calculated. Moreover, if a model of mixed distribution types is necessary, the generalized ICE algorithm (GICE) as disclosed by Delingnon et al., in "Estimation of generalized mixtures and its application in image segmentation" (IEEE Transactions on Image Processing, 6(10):1364-1375, 1997) can be used. GICE generally provides parameter estimates for mixtures composed of a various number and type of statistical distributions.

A fifth non-restrictive illustrative embodiment of the method and device according to the present invention will now be described. For the sake of brevity, only the differences between the fifth and first illustrative embodiments will be described hereinbelow.

In this fifth non-restrictive illustrative embodiment, the segmentation fast marching method allows to treat and analyze, in addition to the volumic information obtained from the boundary layer detections of the blood vessels, dynamic data retrieved from IVUS pullbacks defining a fourth dimension. The dynamic data generally relates to the cyclic pulsation occurring in the blood vessels.

Figure 16:
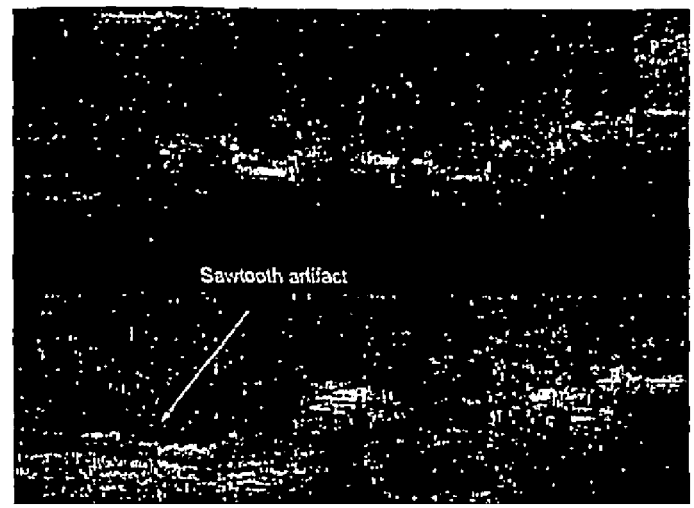
FIG. 16 is a cross-sectional longitudinal view of an IVUS image data showing a sawtooth artifact typically caused by pulsations of blood vessels.

The cyclic variations of the vessel dimensions combined to cardiac motion (for coronary IVUS) was described, in the literature, as the sawtooth artifact which is generally visible on longitudinal view of the IVUS volume and generally caused by the blood vessel pulsations. As shown by the arrow in FIG. 16, the sawtooth artifact is also present in IVUS data of femoral arteries even without cardiac motion. In common femoral arteries for instance, diameter measurements generally vary from 6.8 mm in diastole to 7.2 mm in systole for patients with lower limb peripheral vascular disease, as disclosed by Tai et al. in "In vivo femoropopliteal arterial wall compliance in subjects with and without lower limb vascular disease." (Journal of Vascular Surgery, 30(5):936-945, 1999).

Electrocardiogram-gating (ECG-gating) acquisition was proposed by von Birgelen et al., in "ECG-gated three-dimensional intravascular ultrasound, feasibility and reproducibility of the automated analysis of coronary lumen and atherosclerotic plaque dimensions in humans" (Circulation, 96(9):2944-2952, 1997) to remove this artifact. This is generally accomplished by acquiring 2D IVUS frames at a precise moment of the cardiac cycle, commonly at the end of diastole, which generally gives more accurate and reproducible volumic measurements, as disclosed by von Birgelen et al. and by Bruining et al., in "ECG-gated versus nongated three-dimensional intracoronary ultrasound analysis: Implications for volumetric measurements" (Catheterization, and Cardiovascular Diagnosis, 43:254-260, 1998).

Because ECG-gating hardware is generally not widespread, retrospective gating was proposed to remove the cyclic changes on non-gated IVUS pullback. Change tracking in semi-automatically detected lumen contour was first proposed by Nadkarmi et al., in "Image-based retrospective cardiac gating for three-dimensional intravascular ultrasound imaging" (SPIE Proceedings: Medical Imaging: Ultrasonic Imaging and Signal Processing, volume 4687, pages 276-284, 2002).

Another method searched for cyclic variations in contour features calculated in a pre-processing step as disclosed by de Winter et al., in "Retrospective image-based gating of intra-coronary ultrasound images for improved quantitative analysis: The intelligate method" (Catheterization and Cardiovascular Diagnosis, 61:84-94, 2004). The most recent retrospective gating proposed method is based on variations of the images mean gray level values by Zhu et al., in "Retrieval of cardiac phase from IVUS sequences" (SPIE Proceedings: Medical Imaging: Ultrasonic Imaging and Signal Processing, volume 5035, pages 135-146, 2003) which states that the bigger systolic lumen, that is hypoechoic, generally decreases the mean gray level value of the image.

Some measurements can be made from the cyclic vessel variations. It was demonstrated by Shaw et al., in "Determinants of coronary artery compliance in subjects with and without angiographic coronary artery disease" (Journal of the American College of Cardiology, 39(10):1637-1643, 2002.) that plaque compression is related to the vessel cross-sectional compliance. Also the lumen cross-sectional area (CSA) difference between systolic and diastolic measurements was significantly greater in yellow plaque which generally consists of thin, fibrous cap with lipid-rich core and inadequate collagen content), than white plaque which consists of thick fibrous cap or completely fibrous, as disclosed by Takano et al., in "Mechanical and structural characteristics of vulnerable plaques: Analysis by coronary angioscopy and intravascular ultrasound" (Journal of the American College of Cardiology, 38(1):99-104, 2001).

Thus, the cyclic pulsation contains information about volumic changes of the blood vessel wall that is generally lost when the acquisition is ECG-gated. The vessel pulsation information from non-gated acquisition may be kept and used to reconstruct the vessel wall in 3D, at different moments of the cardiac cycle. With this fourth-dimensional reconstruction of the vessel wall, volumic accuracy and reproducibility can be achieved for measurements made on 3D image sets at specific moments of the cardiac cycle.

To perform 4D reconstruction of the blood vessel wall, detected boundaries from each 2D IVUS frames first have to be classified in different wall pulsation phases. This step may be achieved by searching periodic components in measurements calculated from the detected boundaries.

Figure 17:
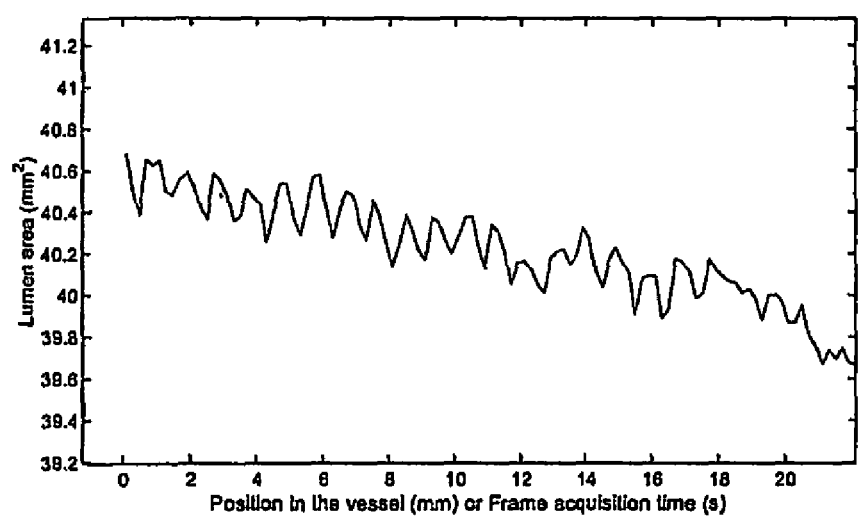
FIG. 17 is a chart view showing layer areas resulting from segmentation detected by a 3D fast marching method based on probability density functions according to a fifth illustrative embodiment of the present invention.

FIG. 17 shows the lumen area calculated from the segmentation results obtained from the semi-automatic PDF-based fast marching method as described hereinabove. A cyclic variation is visible and could be assessed on these retrospective measurements. However, it is also possible to include the wall pulsation assessment in the boundary detection process, such that this information is used to help the segmentation of the IVUS pullback.

The wall pulsation assessment may be initiated during the initial contour calculation procedure (Operation 231 of FIG. 24), and refined when the boundary detection is finished. The wall pulsation is then generally divided in a discrete number of phases (Operation 232 of FIG. 24), such as for example systole, beginning of diastole and end of diastole, and a label is assigned to each wall pulsation phase (Operation 233 of FIG. 24). The pullback 2D IVUS frames are then classified and assigned to the corresponding pulsation phase label (Operation 234 of FIG. 24).

As shown in FIG. 17, the lumen area contains the cyclic pulsation information. Further, the area variation between adjacent frames is generally used to define the classification. Since the pulsation is usually periodic, the cyclic pulsation information is used to deform the initial subset template 158 according to variations of the expected pulsation in the initial contour calculation of individual IVUS images (Operation 215 of FIG. 22). The assignment of the pulsation phase labels to following frames can also take advantage of the periodic information.

At the end of the initialization process, each 2D IVUS frame is identified with a wall pulsation phase label. However, these labels may change because, at the end of the segmentation process, more accurate lumen areas are calculated. The initial labels are therefore adjustable according to their initial value, to the variations in area difference measurements and to the expected value according to the periodic variation (Operation 235 of FIG. 24).

Figure 24:
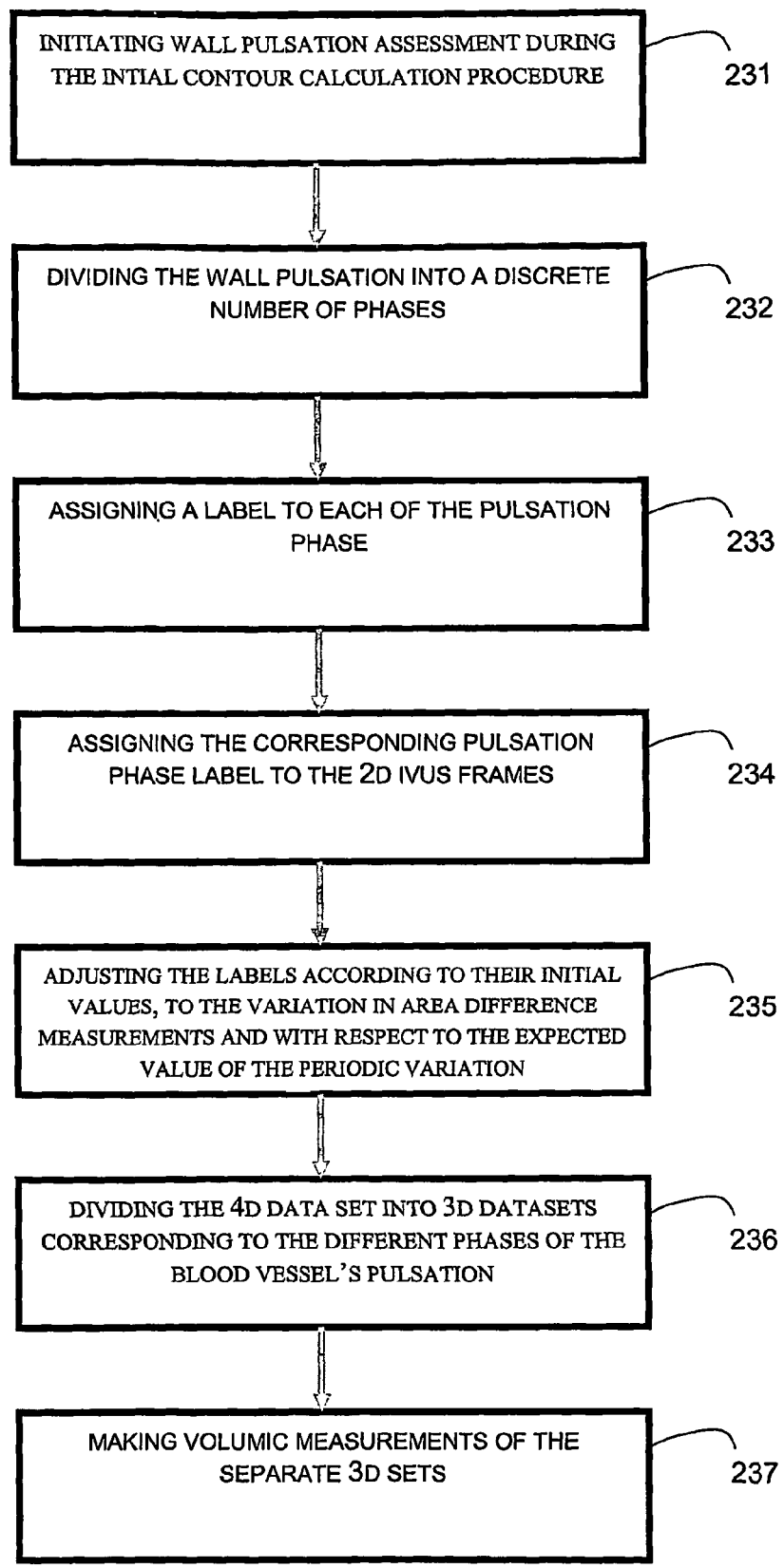
FIG. 24 is a flowchart representing the method for using layer pulsation assessment in the boundary detection segmentation process of the fast-marching method according to the fifth illustrative embodiment of the present invention.

With this pulsation assessment, the 4D data set are divided in 3D data sets composed of all IVUS 2D frames associated to a specific cardiac phase label and corresponding to the different phases of the blood vessel's pulsation (Operation 236 of FIG. 24). Volumic (boundary) measurements can then be made on these separate 3D data sets (Operation 237 of FIG. 24).

Although the present invention has been described hereinabove by way of non-restrictive illustrative embodiments thereof, it can be modified at will, within the scope of the appended claims without departing from the spirit and nature of the subject invention.

What is claimed is:

1. An image segmentation method for estimating boundaries of layers in a multi-layer body, said method comprising:
   providing image data of the multi-layer body using IVUS image data, the image data representing a plurality of image elements;
   determining a plurality of initial interfaces corresponding to regions of the image data to segment; and
   concurrently propagating the initial interfaces corresponding to the regions to segment and thereby estimating the boundaries of the layers of the multi-layer body, propagating the initial interfaces comprising using a fast marching model based on a probability function describing at least one characteristic of the image elements,
   wherein the multi-layer body is a multi-layer blood vessel.

2. An image segmentation method as defined in claim 1, wherein:
   determining each initial interface comprises defining the initial interface as a zero level of a given function; and
   propagating each initial interface comprises moving the given function according to a speed function.

3. An image segmentation method as defined in claim 1, wherein the image elements comprise pixels and wherein the fast marching model is based on a probability density function estimating a color map of the pixels for each region of the image data.

4. An image segmentation method as defined in claim 1, wherein the image elements comprise pixels and wherein the fast marching model is based on a gradient function estimating a color map of the pixels for each region of the image data.

5. An image segmentation method as recited in claim 1, wherein determining each initial interface comprises:
   manually tracing an initialization contour in a longitudinal plane of the IVUS image data;
   transposing reference points of the initialization contour to intersecting IVUS 2D frames of the IVUS image data; and
   defining the initial interface from the transposed reference points in the IVUS 2D frames.

6. An image segmentation method as defined in claim 5, wherein defining the initial interface comprises tracing shrunk contours from an interface passing by the reference points.

7. An image segmentation method as recited in claim 5, wherein manually tracing an initialization contour comprises tracing a plurality of initialization contours.

8. An image segmentation method as recited in claim 7, wherein transposing reference points of the initialization contour comprises transposing reference points from the plurality of initialization contours.

9. An image segmentation method as recited in claim 1, wherein:
   the image elements comprise pixels each having a color map; and
   using a fast marching method comprises estimating a color map of pixels in each of the regions to segment in the IVUS 2D frames of the IVUS image data using a mixture of probability density functions.

10. An image segmentation method as defined in claim 9, wherein the probability density functions comprise Rayleigh probability density functions.

11. An image segmentation method as defined in claim 9, wherein the probability density functions comprise Gaussian probability density functions.

12. An image segmentation method as recited in claim 9, wherein using a mixture of probability density functions comprises determining an occurring probability value of the gray levels of the pixels.

13. An image segmentation method as recited in claim 9, wherein using a mixture of gray level probability density functions comprises iteratively finding mixture parameters via an Expectation Maximization (EM) algorithm, comprising:
 a) calculating a cost function given an observed value of said color map and a previous estimate of said mixture parameters;
 b) maximizing said cost function to analytically evaluate a new estimate of said mixture parameters;
 c) initializing said previous estimate of said mixture parameters to said new estimate of said mixture parameter if both are different; and
 d) repeating a) to c) until said previous estimate of said mixture parameters is the same as said new estimate of said mixture parameters.

14. An image segmentation method as recited in claim 1, wherein propagating the initial interfaces comprises constructing an arrival time function algorithm, comprising:
 a) defining a speed function for the initial interfaces in terms of said probability function;
 b) propagating the interface by selecting an interface point having a smallest arrival time;
 c) calculating the arrival time and speed function of neighbors of the interface point; and
 d) repeating a) to c) until the propagating initial interfaces have all propagated across the regions to segment.

15. An image segmentation method as recited in claim 14, wherein repeating a) to c) is performed until the propagating initial interfaces are stationary.

16. An image segmentation method as recited in claim 14, wherein said neighbors comprises a number of pixels located around the interface point having the smallest arrival time.

17. An image segmentation method as recited in claim 1, wherein providing IVUS image data comprises pulling back in the multi-layer blood vessel a catheter equipped with an IVUS image data acquisition tool.

18. An image segmentation method as recited in claim 1, wherein providing IVUS image data comprises:
 a) acquiring IVUS data;
 b) digitizing image data from the IVUS data on a pixel matrix;
 c) storing the pixel matrix in 2D IVUS frames; and
 d) calculating an estimation of mixture parameters of a probability density function forming said probability function.

19. An image segmentation method as recited in claim 1, wherein providing IVUS image data comprises:
 a) acquiring in-vivo 2D IVUS frames;
 b) generating segmented contours by tracing initialization contours on longitudinal planes of said IVUS image data and transposing reference points of said initialization contours on said segmented contours; and
 c) applying an image-formation model to said segmented contours generating simulated 2D IVUS frames.

20. An image segmentation method as recited in claim 19, wherein applying an image formation model comprises:
 a) applying an acoustic impedance variations function to the segmented contours;
 b) expressing said acoustic impedance variations function in polar coordinates;
 c) processing said acoustic impedance variations function in polar coordinates with a polar spread function via a 2D convolution operator generating a polar radio-frequency image;
 d) expressing said radio-frequency image in polar B-mode image; and
 e) generating said simulated 2D IVUS frames by expressing said polar B-mode image in Cartesian coordinates.

21. An image segmentation method for estimating boundaries of layers in a multi-layer body, said method comprising:
 a) providing image data of the multi-layer body using IVUS image data, the image data representing a plurality of image elements;
 b) determining a plurality of initial interfaces corresponding to regions of the image data to segment; and
 c) concurrently propagating the initial interfaces corresponding to the regions to segment said regions and estimate the boundaries of the layers of the multi-layer body, propagating the initial interfaces comprising using a fast marching model based on a gradient function describing at least one characteristic of the image elements,
 wherein the multi-layer body is a multi-layer blood vessel.

22. An image segmentation method as defined in claim 21, wherein the image elements comprises pixels having a gray level, and wherein the fast marching model is based on a gray level gradient function of the pixels for each region of the image data.

23. An image segmentation method as recited in claim 1, wherein providing IVUS image data comprises undersampling an initial resolution of said IVUS image data in l resolution levels of IVUS 2D frames, each resolution levels being a $2^l$ fraction of said initial resolution of said IVUS image data.

24. An image segmentation method as recited in claim 23, wherein propagating the initial interfaces according to a fast-marching model comprises:
 a) estimating probability functions in the IVUS image data for obtaining image segmentation results of a first lowest resolution level amongst remaining l resolution levels;
 b) mapping the segmentation results into a second lowest resolution level amongst remaining l resolution levels; and
 c) repeating a) and repeating b) until the first lowest resolution level is said initial resolution level of said IVUS image data.

25. An image segmentation method as recited in claim 1, wherein providing IVUS image data comprises generating l scale levels of IVUS 2D frames from an initial scale of said IVUS image data, each scale level being a function of a $2^l \times 2^l$ portion of said initial scale of said IVUS image data.

26. An image segmentation method as recited in claim 25, wherein propagating the initial interfaces according to a fast-marching model comprises:
 a) estimating probability functions in the IVUS image data for obtaining image segmentation results of a first highest scale level amongst remaining l scale levels;
 b) mapping the segmentation results into a second highest scale level amongst remaining l scale levels; and
 c) repeating a) and repeating b) until the first highest scale level is said initial scale level of said IVUS image data.

27. An image segmentation method as recited in claim 1, wherein determining a plurality of initial interfaces comprises:
 a) selecting a subset of contiguous 2D IVUS frames from said IVUS image data;
 b) generating initial interfaces of an inner-layer region estimating an inner layer of the multi-layer blood vessel;

c) searching an initial interface of a side layer of the vessel from said inner-layer region;

d) calculating a likelihood map for said side layer and growing a side-layer region from said map; and e) fitting said inner-layer region and said side-layer region on each contiguous 2D IVUS frames of said subset.

28. An image segmentation method as recited in claim 1, wherein using a mixture of gray level probability density functions comprises iteratively finding mixture parameters via a parameter estimation algorithm comprising:

a) simulating realizations of a hidden data information according to a posterior distribution;

b) calculating an estimate of said mixture parameters with a parameter estimator;

c) repeating a) and b) until convergence of said mixture parameters.

29. An image segmentation method as defined in claim 1, wherein the image data comprises B-mode IVUS image.

30. An image segmentation method as defined in claim 1, wherein the image data comprises RF IVUS image.

31. An image segmentation method as defined in claim 1, wherein the fast marching model is based on a probability function estimating the gray level distribution of pixels of the image data.

\* \* \* \* \*